US012749584B1

(12) United States Patent
Jukic et al.

(10) Patent No.: US 12,749,584 B1
(45) Date of Patent: Sep. 29, 2026

(54) SYSTEM AND METHOD FOR GOVERNED CLINICAL REASONING AND INSIGHT GENERATION USING ARTIFICIAL INTELLIGENCE

(71) Applicant: OneSource Solutions International, Inc., Sudbury, MA (US)

(72) Inventors: Vedran Jukic, Trieste (IT); Harold Arkoff, Sudbury, MA (US)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/441,077

(22) Filed: Jan. 6, 2026

Related U.S. Application Data

(63) Continuation-in-part of application No. 19/271,679, filed on Jul. 16, 2025, now Pat. No. 12,542,216.

(51) Int. Cl.
*G16H 50/20* (2018.01)

(52) U.S. Cl.
CPC .................................. *G16H 50/20* (2018.01)

(58) Field of Classification Search
CPC ...................................................... G16H 50/20
USPC .......................................................... 705/2–3
See application file for complete search history.

(56) References Cited

U.S. PATENT DOCUMENTS 9,465,778 B1 * 10/2016 DeBo ...................... G06F 16/21
11,315,669 B1 * 4/2022 Friedman ............... G06N 5/025
11,775,904 B1 * 10/2023 Sanni ................. G06Q 10/0635 705/7.28
12,001,464 B1 * 6/2024 Arkoff ................ G06F 16/3334
12,002,579 B1 * 6/2024 Arkoff ................... G16H 40/20
12,242,433 B2 * 3/2025 Gottlob ................. G06F 16/211
12,337,143 B1 * 6/2025 Arkoff ................... G16H 40/63
12,445,308 B1 * 10/2025 Arkoff .................. H04L 9/3247
2002/0012899 A1 * 1/2002 Finitzo .................. A61B 5/121 434/262
2004/0025030 A1 * 2/2004 Corbett-Clark ........ G16H 10/40 713/186
2004/0177090 A1 * 9/2004 Corbett-Clark ..... G06F 16/9024
(Continued)

*Primary Examiner* — Michael Tomaszewski
(74) *Attorney, Agent, or Firm* — IP Consulting Group; Michael Razavi; Alfred F. Hoyte, Jr.

(57) ABSTRACT

Systems and methods are disclosed for generating governed clinical insights through real-time clinician interaction. The disclosed platform integrates a medical data governance engine with orchestrated artificial intelligence reasoning components to prepare, contextualize, and govern patient-related data prior to use by one or more reasoning models. Clinician interaction may occur through voice-based and multimodal conversational interfaces that transform continuous interaction into structured, serialized inputs for governed processing. A supervisory orchestration component coordinates execution of modular artificial intelligence agents and large language models based on clinical context and temporal scope. Candidate outputs are subjected to non-bypassable validation and authorization by a validation arbiter before any presentation to a clinician or downstream system. The architecture enforces governance, safety, provenance, and compliance constraints across heterogeneous data sources, reasoning components, and interaction modalities, enabling timely, context-aware clinical insights while preventing exposure of ungoverned data or unvalidated outputs.

28 Claims, 8 Drawing Sheets

System architecture overview, illustrating representative components and interactions of an insight platform in an example embodiment

(56) References Cited

U.S. PATENT DOCUMENTS

2007/0061393 A1* 3/2007 Moore .................... H04L 67/02 709/201
2009/0080408 A1* 3/2009 Natoli ................... G06F 16/258 370/351
2010/0023346 A1* 1/2010 Paty ................... G06Q 30/0203 705/2
2013/0096943 A1* 4/2013 Carey .................... G16B 50/40 705/2
2014/0379379 A1* 12/2014 Janevski ................ G16H 50/20 705/3
2016/0196516 A1* 7/2016 Anisingaraju ..... G06Q 10/0635 705/7.28
2016/0210427 A1* 7/2016 Mynhier ................ G16H 10/60
2018/0165416 A1* 6/2018 Saxena .................. G16H 50/20
2018/0322110 A1* 11/2018 Rhodes ............... G06F 16/3344
2019/0188294 A1* 6/2019 Mackenthun ..... G06F 16/24564
2020/0051698 A1* 2/2020 Chan ...................... G16H 10/60
2021/0050104 A1* 2/2021 Arkoff .................. G06F 21/602
2023/0075525 A1* 3/2023 Naqvi ................... H04L 9/0822
2023/0197214 A1* 6/2023 Arkoff ................... G16H 10/60 705/3
2023/0342700 A1* 10/2023 Perkins ............ G06Q 10/06395
2023/0394036 A1* 12/2023 Mackenthun ......... G06F 16/122
2023/0395243 A1* 12/2023 Teeple ................... G16H 40/20
2024/0096460 A1* 3/2024 Arkoff ................... G16H 40/67
2024/0303235 A1* 9/2024 Kulkarni ........... G06F 16/24522
2024/0362208 A1* 10/2024 Naufel .................. G06F 16/243
2024/0387014 A1* 11/2024 Kumar Karn .......... G16H 15/00
2024/0420124 A1* 12/2024 Ramde ................ G06F 21/6245
2025/0053687 A1* 2/2025 Blum .................. G06F 21/6254
2025/0094628 A1* 3/2025 McDonnell ........... G06F 21/604
2025/0131188 A1* 4/2025 Towles .................. G06F 40/186
2025/0238447 A1* 7/2025 Arkoff ................ G06F 21/6245
2025/0246317 A1* 7/2025 Vesto ..................... G16H 10/60
2025/0307418 A1* 10/2025 Spencer ................ G06F 21/577
2025/0372244 A1* 12/2025 Jukic ...................... G16H 10/60
2025/0378155 A1* 12/2025 Manton ............... G06F 11/3476
2026/0019268 A1* 1/2026 Arkoff ................... G16H 10/60
2026/0023842 A1* 1/2026 Neystadt ................. G06F 21/45
2026/0024668 A1* 1/2026 Arkoff ................... G16H 50/30
2026/0121859 A1* 4/2026 Arkoff ................ G06F 21/6245

* cited by examiner

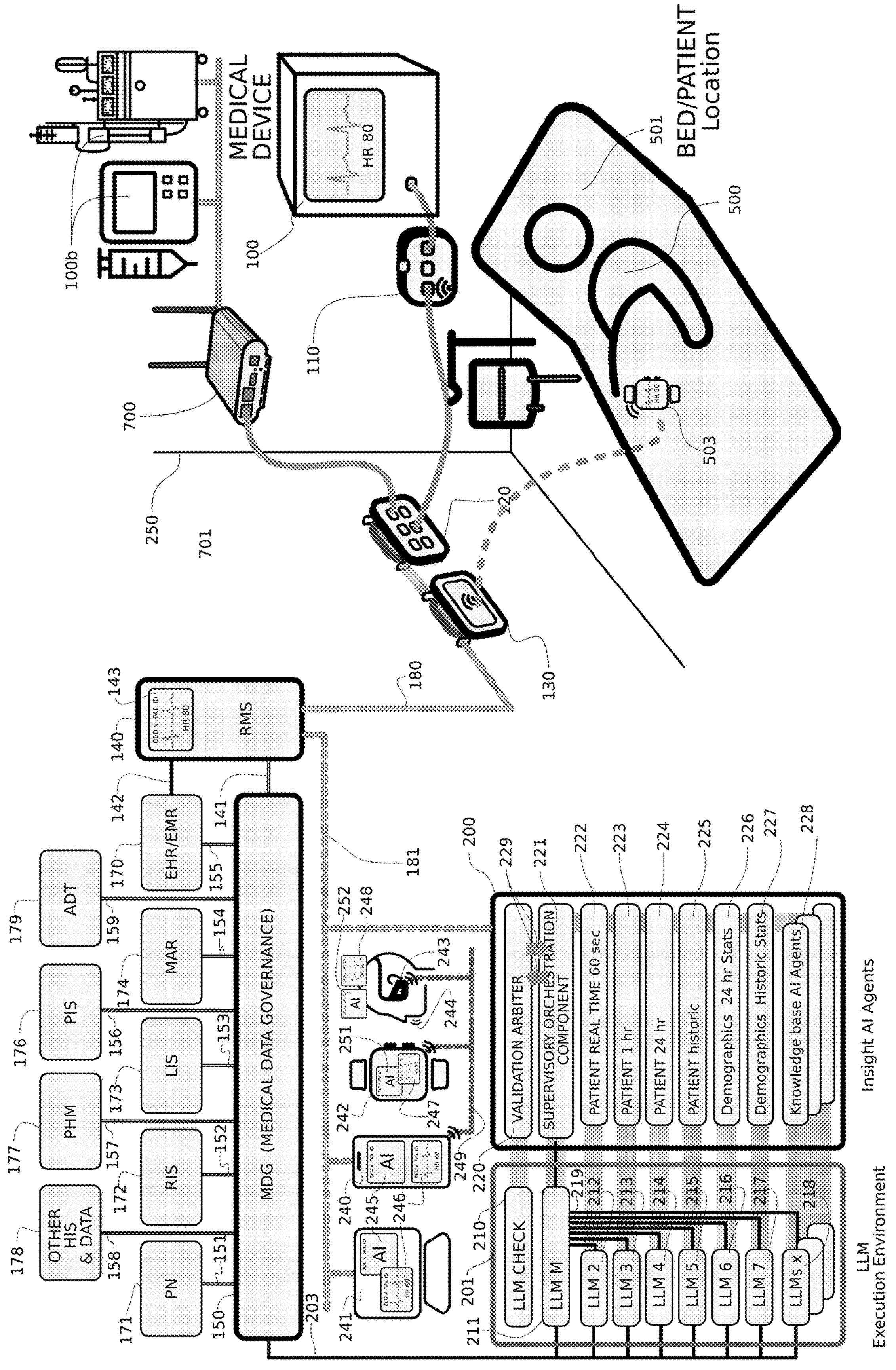
FIG. 1: System architecture overview, illustrating representative components and interactions of an insight platform in an example embodiment

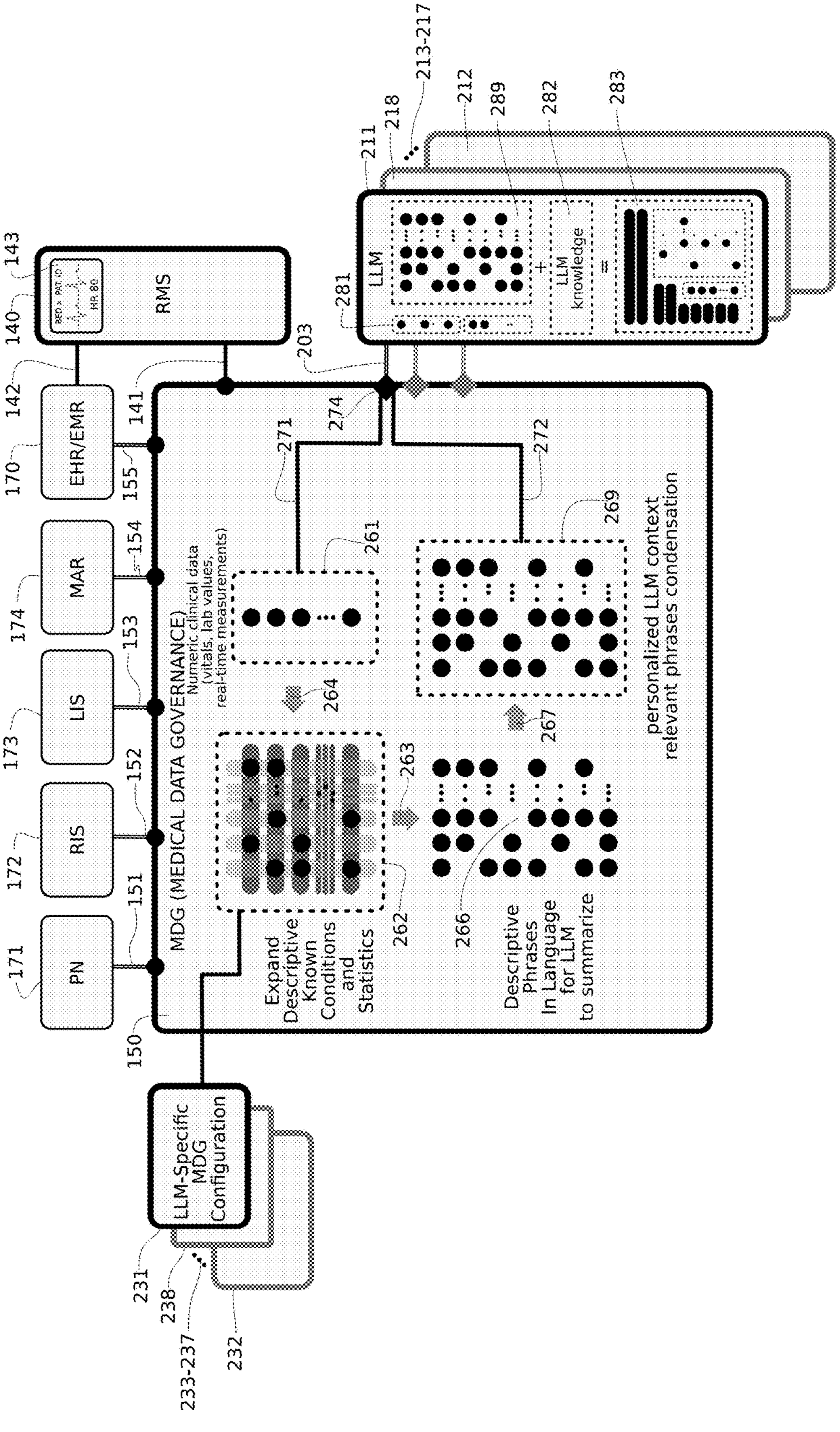
FIG. 2: LLM-MDG interaction workflow, illustrating governance-controlled expansion, condensation, and contextualization of patient data in an example embodiment.

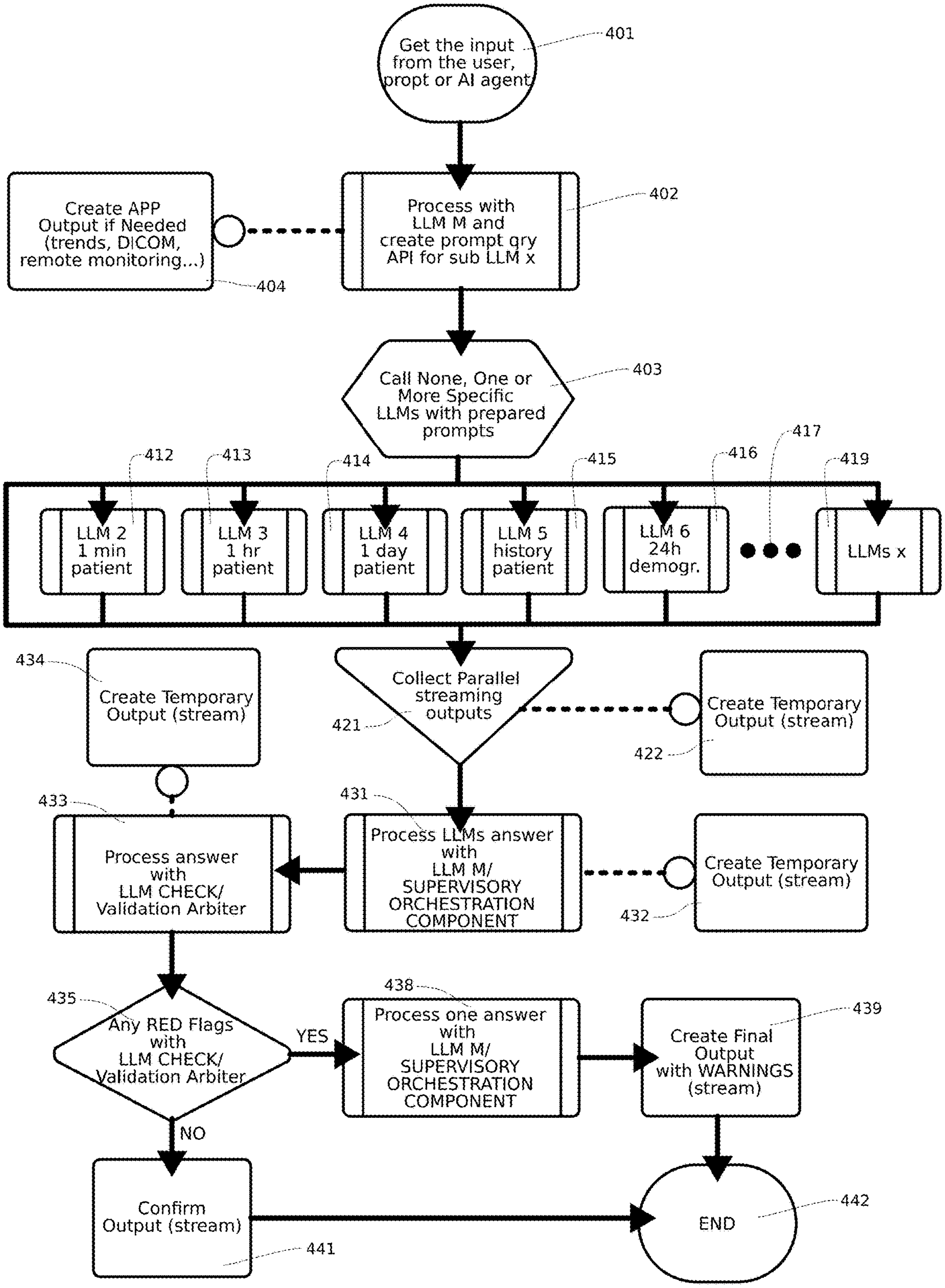
FIG. 3: Query processing workflow, illustrating orchestration, parallel reasoning, validation, and delivery of clinician-initiated requests in an example embodiment.

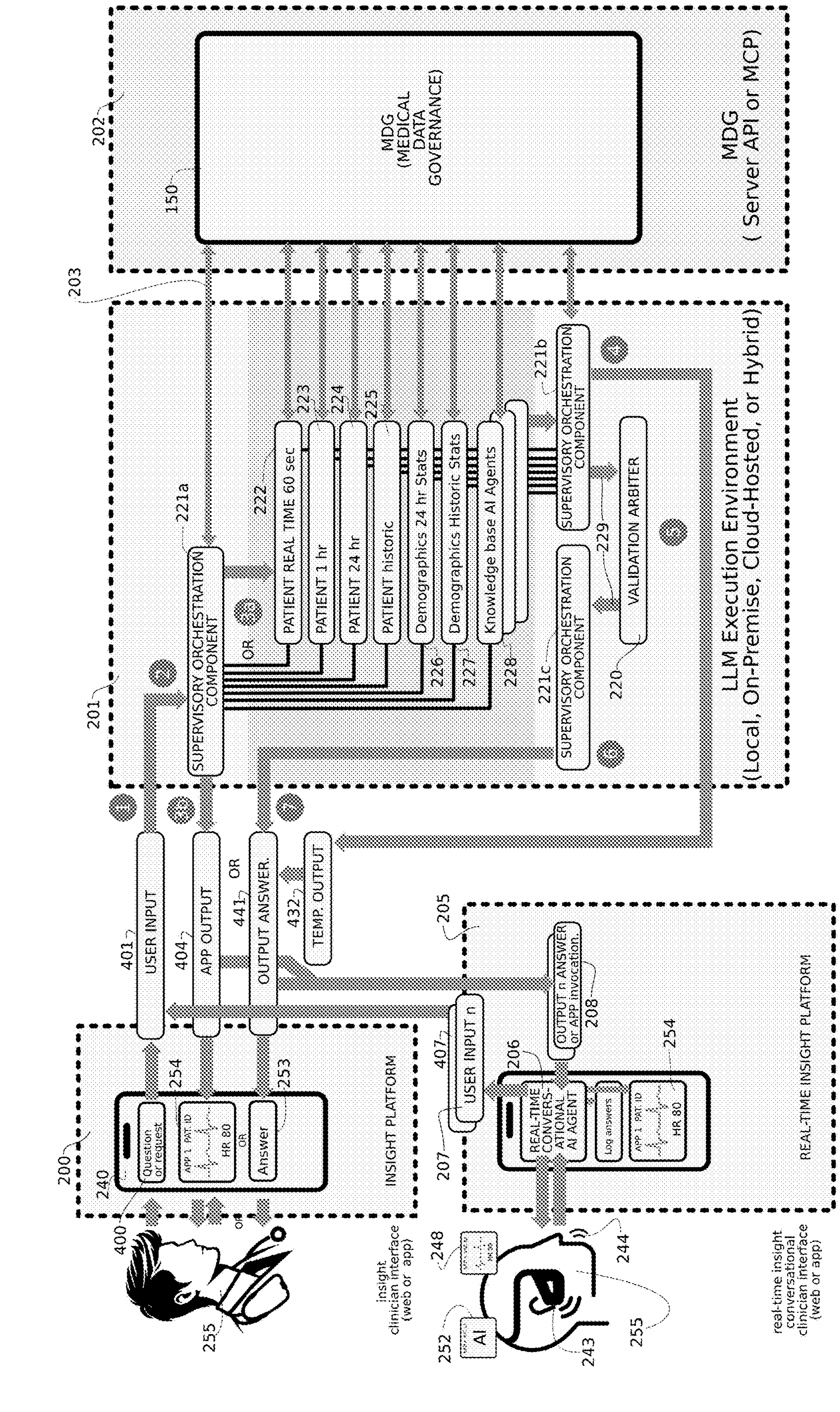
FIG. 4: Modular AI agent collaboration architecture, illustrating serialized clinician interaction, governed reasoning, validation, and output delivery in an example embodiment.

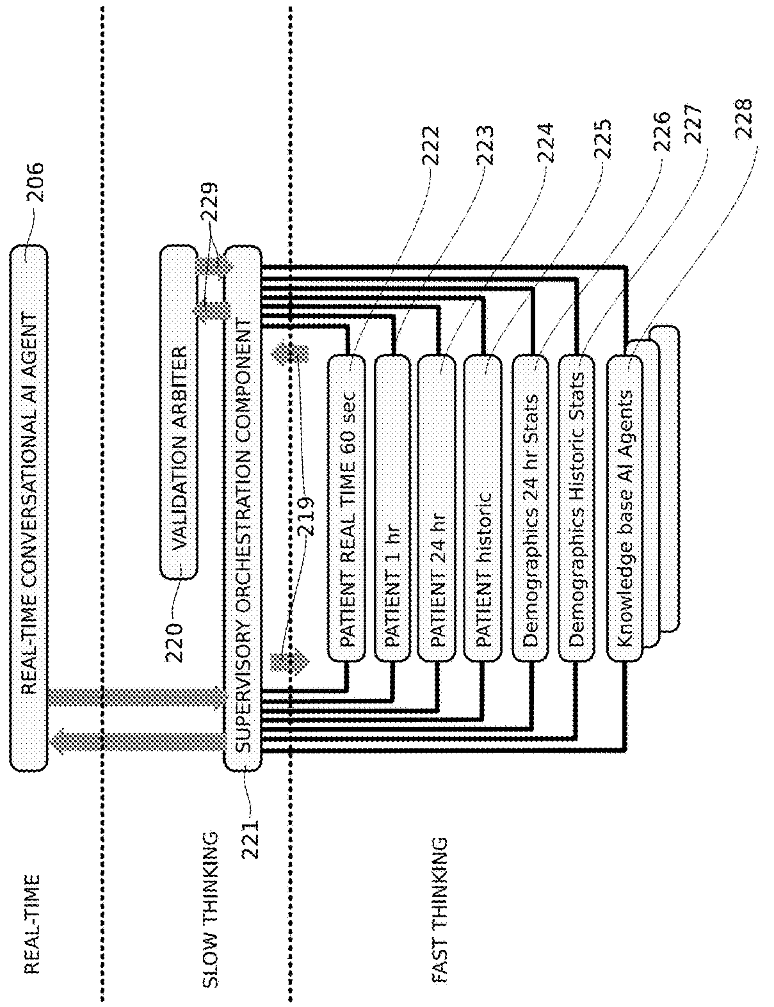
FIG. 5: Dual-layer AI processing architecture, illustrating coordinated fast-thinking and slow-thinking operations with real-time conversational mediation in an example embodiment.

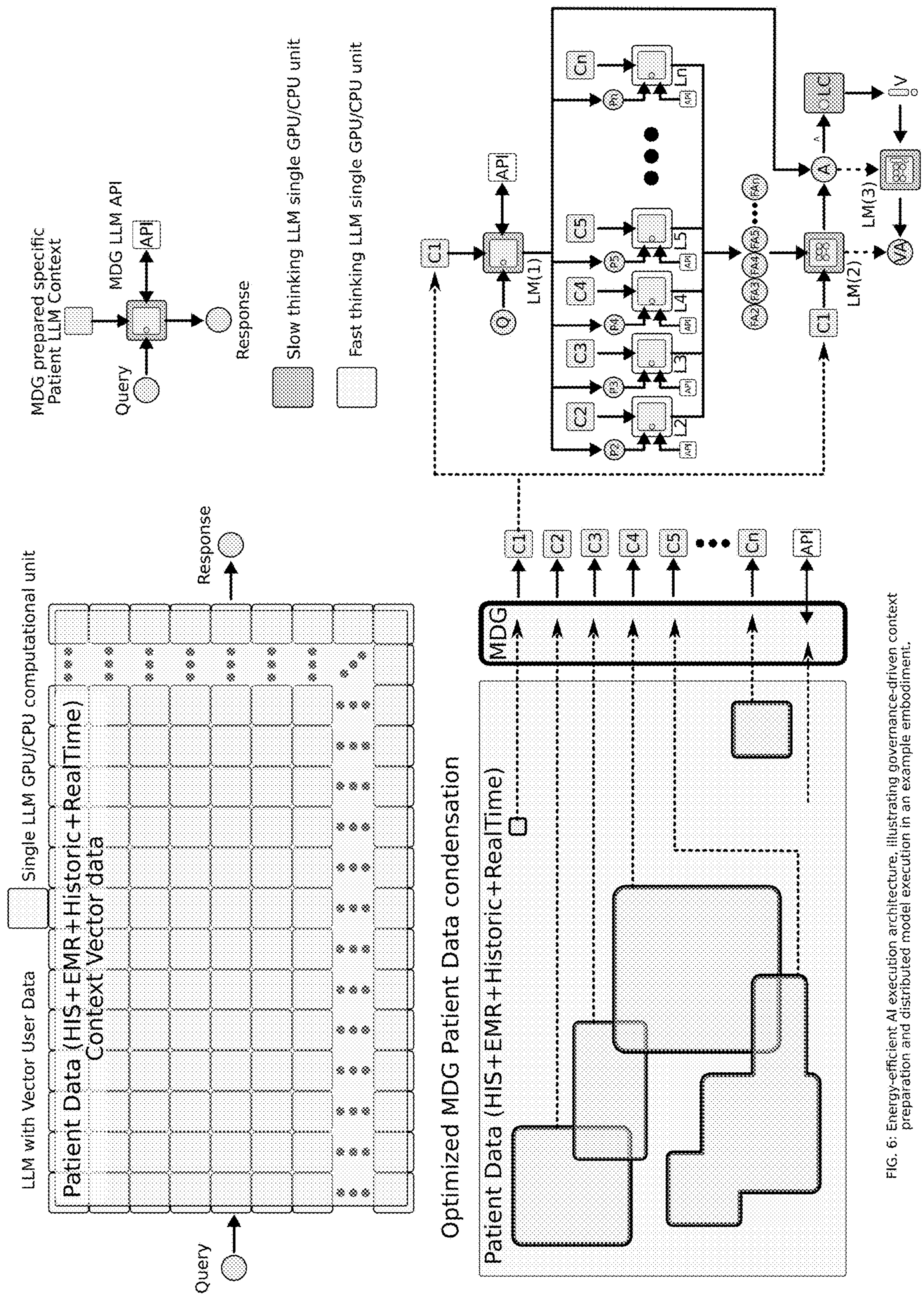
FIG. 6: Energy-efficient AI execution architecture, illustrating governance-driven context preparation and distributed model execution in an example embodiment.

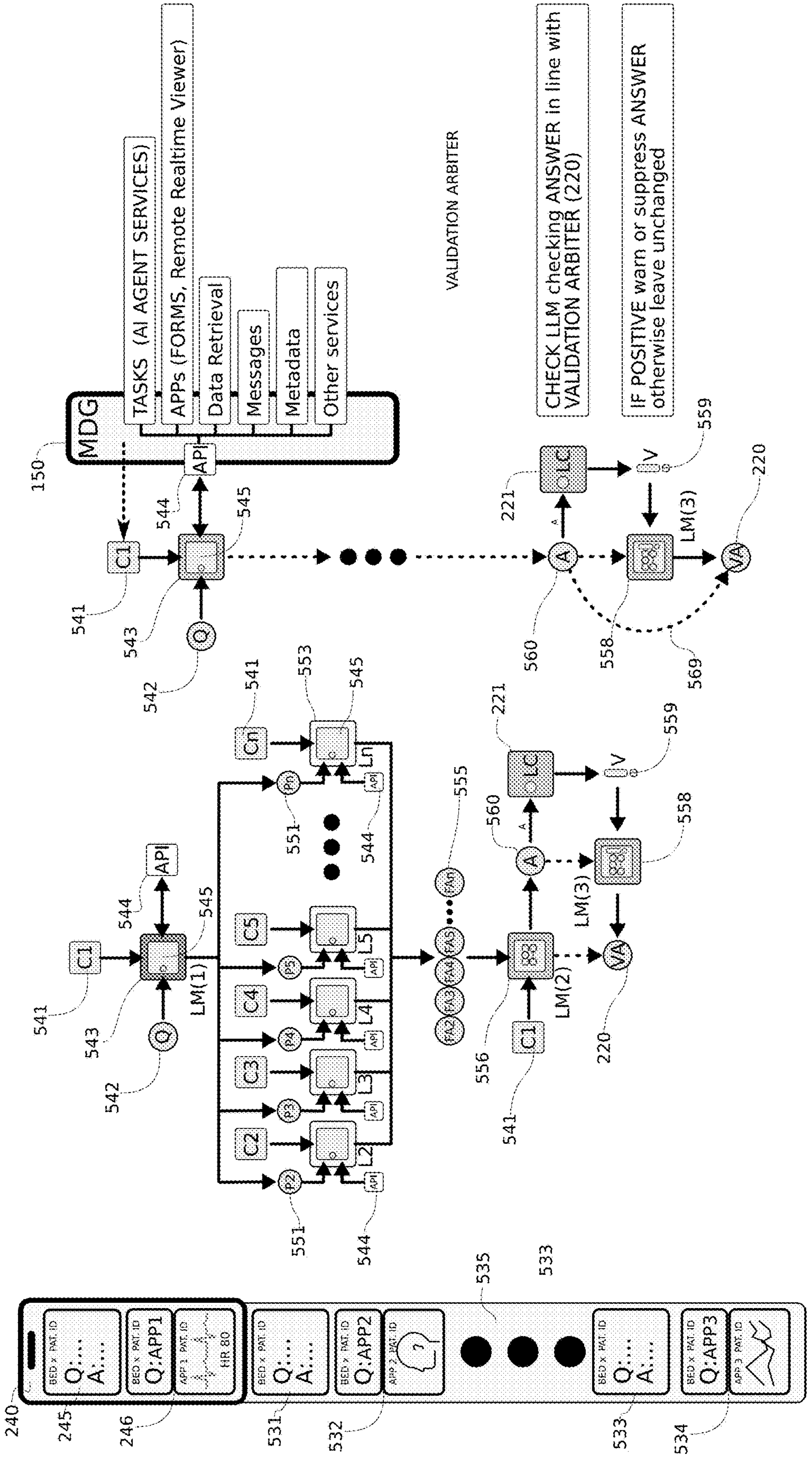
FIG. 7: Governed output delivery and task execution workflow, illustrating validated insight delivery and application coordination in an example embodiment.

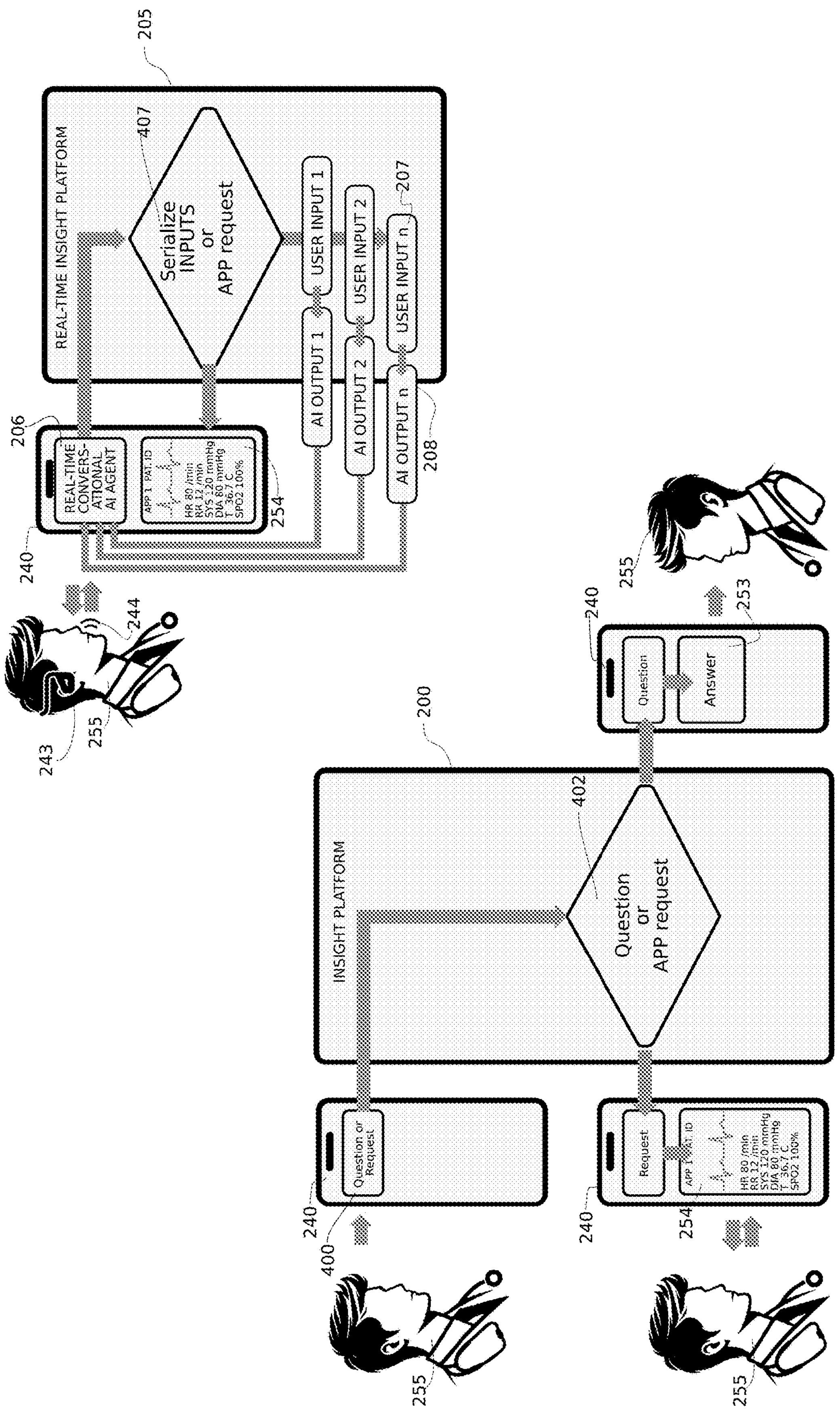
FIG. 8: On-demand, context-aware insight generation workflow, illustrating unified interaction, request classification, and application delivery in an example embodiment.

SYSTEM AND METHOD FOR GOVERNED CLINICAL REASONING AND INSIGHT GENERATION USING ARTIFICIAL INTELLIGENCE

CROSS-REFERENCE TO RELATED APPLICATIONS

This application is a continuation-in-part of U.S. Non-Provisional patent application Ser. No. 19/271,679, entitled "Personalized AI Agent as a Case Manager," filed on Jul. 16, 2025, which has been allowed and is expected to issue as a United States patent.

application Ser. No. 19/271,679 claims the benefit of priority to U.S. Provisional Patent Application No. 63/672,870, filed on Jul. 18, 2024.

This application further claims the benefit of priority, under 35 U.S.C. § 119 (e), to:

- U.S. Non-Provisional application Ser. No. 19/439,917 filed on Jan. 5, 2026 entitled "Systems and Methods for Governed Release of Clinical Outputs Generated by Automated Reasoning".
- U.S. Provisional Patent Application No. 63/742,081, filed on Jan. 6, 2025, entitled "AI Keystone System for Advanced Medical Decision Support and Scalable On-Demand Clinical Insights"; and
- U.S. Provisional Patent Application No. 63/780,190, filed on Mar. 29, 2025, entitled "System and Method for Real-Time Clinical Insight Using AI-Driven Medical Data Governance."

The disclosures of each of the foregoing applications are hereby incorporated by reference for purposes of priority, support, and optional embodiments, and not to import limitations inconsistent with the present disclosure.

Subject matter disclosed and claimed herein that is supported by the disclosure of U.S. Provisional Patent Application No. 63/672,870 is entitled to the priority date of Jul. 18, 2024. Subject matter supported by the disclosure of U.S. Provisional Patent Application No. 63/742,081 is entitled to the priority date of Jan. 6, 2025. Subject matter first disclosed in U.S. Provisional Patent Application No. 63/780,190 is entitled to the priority date of Mar. 29, 2025.

This application is also related to U.S. Pat. Nos. 11,309,665 B1, 11,693,990 B1, and 12,001,464 B1, and to U.S. Provisional Patent Application No. 62/804,838, which describe medical device connectivity, medical data governance, and large-language-model-based medical data transformation; these documents are incorporated herein by reference solely for purposes of background, illustrative context, and optional embodiments, and not for the purpose of importing structural, architectural, hardware, or deployment limitations into the present disclosure, except where such features are expressly and explicitly recited herein.

In the event of any inconsistency between the present disclosure and any incorporated reference, the present disclosure shall control.

FIELD OF THE INVENTION

The present invention relates generally to healthcare information systems and artificial intelligence-assisted clinical computing, and more particularly to systems and methods for governed acquisition, contextualization, orchestration, validation, and delivery of patient-related clinical information and insights in response to clinician interaction.

In various embodiments, the invention pertains to an integrated software platform that coordinates Medical Data Governance, context preparation, multi-model artificial intelligence reasoning, and non-bypassable validation and authorization controls to support clinician interaction with patient-specific information through natural language queries, application invocation, real-time conversational interaction, or other interaction modalities. The disclosed systems and methods operate across heterogeneous clinical data sources, computing environments, and user interfaces, while enforcing governance, safety, and compliance constraints prior to delivery of any system output.

Unlike conventional healthcare information systems that primarily function as static repositories, alerting engines, or reference tools, the invention addresses the technical challenge of enabling context-aware, patient-specific reasoning over dynamically evolving clinical data including clinician-originated conversational input, without exposing ungoverned data to artificial intelligence models or permitting unvalidated outputs to reach clinicians. To this end, the invention introduces an architecture in which governed clinical context is prepared, scoped, and selectively supplied to one or more reasoning components, the resulting outputs of which are subject to explicit validation and authorization prior to presentation or downstream use.

In some embodiments, the invention supports interactive clinician workflows in which a clinician may submit requests, queries, or instructions using natural language or other interaction modalities, including real-time, multimodal conversational interfaces, and the system dynamically determines whether to generate an informational response, invoke a clinical application, coordinate a task, or perform other governed system actions. The invention further supports concurrent workflows, multi-application contexts, interruptible and serialized conversational interaction, and longitudinal interaction, while maintaining auditability, provenance, and policy enforcement across all stages of data handling and reasoning.

The field of the invention thus encompasses governed clinical reasoning platforms, validation-constrained artificial intelligence systems, real-time conversational clinician interaction systems, and context-aware healthcare computing architectures that operate as intermediaries between clinicians, patient data, and downstream clinical services. The disclosed invention is applicable across a wide range of care settings, clinical specialties, and deployment environments, and is not limited to any particular medical device, data source, artificial intelligence model, or user interface technology.

BACKGROUND OF THE INVENTION

Contemporary healthcare environments generate large volumes of patient-related information originating from numerous heterogeneous sources, including electronic healthcare information systems, laboratory and imaging systems, administrative systems, and real-time or near-real-time monitoring devices. While such data is essential to clinical workflows, it is often distributed across disparate systems, stored in differing formats, governed by distinct access rules, and exposed through inconsistent interfaces. As a result, clinicians are frequently required to navigate multiple applications, perform repeated authentication steps, and manually synthesize information from siloed data sources in order to obtain a coherent view of a patient's condition.

Existing electronic health record systems and hospital information systems primarily function as repositories for documentation and transactional data entry. Although such systems may provide alerts, dashboards, or predefined reports, they typically lack mechanisms for dynamically preparing patient-specific context across systems or for selectively constraining data exposure based on the intent and scope of a particular clinical request. Fragmentation, latency, and limited interoperability among systems can increase cognitive burden, delay access to relevant information, and complicate clinical workflows, particularly in time-sensitive or high-complexity care settings.

As the scale, velocity, and diversity of healthcare data continue to increase, manual review and interpretation of patient information becomes increasingly impractical at the point of care. Conventional clinical decision support tools have attempted to address this challenge through rules-based alerts, static guideline references, or narrowly scoped dashboards. However, such approaches are often rigid, difficult to adapt to evolving clinical contexts, and limited in their ability to incorporate real-time data, longitudinal history, or role-specific perspectives. Moreover, many existing systems do not provide a systematic way to govern how data is prepared, scoped, or validated prior to use in downstream reasoning or presentation.

Recent advances in artificial intelligence, including natural language processing and large language models, have enabled general-purpose digital assistants capable of interpreting user instructions and interacting with multiple applications. While such technologies demonstrate utility in consumer and enterprise domains, they typically operate on loosely governed data substrates and are not designed to enforce the access control, provenance tracking, contextual scoping, auditability, and validation requirements necessary for use in regulated clinical environments. In particular, the generation of unvalidated or non-contextualized outputs presents technical and regulatory challenges when applied to patient-related information.

Efforts to incorporate artificial intelligence into healthcare computing systems have further been constrained by concerns related to data governance, explainability, consistency, security, and regulatory compliance. Integrating advanced reasoning models into clinical workflows without exposing ungoverned data, permitting unauthorized inference, or allowing unvalidated outputs to influence clinical activity remains a significant technical challenge. Existing solutions often address isolated aspects of this problem but lack an integrated architecture that coordinates governed data preparation, multi-stage reasoning, and non-bypassable validation prior to output delivery.

Accordingly, there exists a need for systems and methods that enable clinicians to interact with patient-related information in a flexible and efficient manner while maintaining strict governance, safety, and compliance controls. Such systems should be capable of harmonizing data from diverse sources, preparing context appropriate to a specific request or task, invoking advanced reasoning techniques without exposing ungoverned data, and ensuring that any outputs are subject to explicit validation and authorization prior to presentation or downstream use. It would further be desirable for such systems to operate across heterogeneous deployment environments, integrate with existing clinical systems through defined interfaces, and support concurrent workflows without imposing rigid interaction models.

The present invention is directed to addressing these and other technical challenges by providing a governed clinical computing architecture that integrates medical data governance, context preparation, artificial intelligence reasoning, validation, and delivery into a coordinated platform. By structuring how patient-related data is accessed, contextualized, reasoned over, and authorized, the invention enables interactive clinician workflows while preserving auditability, policy enforcement, and system-level safety constraints across a wide range of healthcare settings.

SUMMARY OF THE INVENTION

The present invention provides systems and methods for governed clinical computing that enable interactive, real-time, context-aware reasoning over patient-related data while enforcing policy, validation, and authorization controls prior to output delivery. The invention is directed to a software-centric architecture that coordinates medical data governance, artificial intelligence-based reasoning, supervisory orchestration, multi-stage validation, and clinician interaction within a unified platform, referred to herein as an insight platform.

In accordance with the invention, patient-related information originating from heterogeneous electronic healthcare information systems, monitoring systems, medical devices, and other data sources is received and processed under control of a Medical Data Governance (MDG) engine. The MDG engine enforces access control, contextual scope, provenance, temporal alignment, and auditability, and prepares governed, context-constrained data representations tailored to specific analytical tasks or clinician requests. These governed context representations are selectively supplied to downstream reasoning components without exposing raw or ungoverned data.

Clinician interaction with the system occurs through one or more clinician-facing interfaces that may include real-time conversational interaction modalities, such as voice-based and multimodal input, as well as visual or application-based interaction. In some embodiments, clinician interaction is mediated by a real-time conversational interaction component configured to maintain an active conversational session with the clinician, handle interruptions and follow-on requests, manage prioritization, and dynamically assess whether received input is complete or contextually sufficient. When conversational input is incomplete or ambiguous, the system may request additional information prior to initiating governed reasoning.

To ensure that continuous conversational interaction does not bypass governance or validation controls, conversational input is not forwarded directly for reasoning. Instead, conversational input is transformed by an input serialization and sequencing process into a series of discrete, ordered user input units. Each serialized input unit is processed independently under governance control, and corresponding candidate outputs are generated and evaluated on a per-unit basis. This serialization mechanism preserves conversational ordering, interruption handling, and deferred requests while preventing reordering, output interleaving, or bypass of orchestration and validation mechanisms.

In some embodiments, the system further supports governed ambient conversational capture, in which clinician-patient or clinician-clinician audio is continuously or opportunistically captured, transcribed, and segmented into structured user input units for processing under the same orchestration and validation controls.

Upon receipt of a serialized user input unit or system-initiated task, a supervisory orchestration component interprets the request, determines applicable clinical context and temporal scope, and coordinates invocation of one or more reasoning components. The reasoning layer may include large language models and specialized artificial intelligence agents configured for different analytical roles, temporal horizons, or data granularities. Requests may be decomposed, routed, and processed in parallel, and intermediate analytical outputs may be aggregated or synthesized under orchestration control.

In some embodiments, reasoning is performed using a combination of fast-response processing components optimized for low-latency analysis and slow-response processing components configured for deeper contextual evaluation, cross-checking, and assurance. Candidate clinical outputs generated by the reasoning layer are not delivered directly to clinicians. Instead, such outputs are routed to a validation arbiter that evaluates each candidate output against defined safety, governance, compliance, and consistency criteria. The validation arbiter enforces non-bypassable release semantics and may optionally invoke one or more checking language models to independently assess candidate outputs prior to authorization.

Only candidate outputs that satisfy validation and authorization requirements are released as authorized clinical outputs. Authorized outputs may be presented through a clinician-facing interface in a modality consistent with the originating interaction, including conversational output, visual presentation, or application-driven output. In conversational embodiments, authorized outputs are delivered in an ordered manner corresponding to the serialized input units, ensuring coherent conversational flow while maintaining governance and validation guarantees. The system maintains contextual binding between inputs, outputs, patient context, and workflow state to support traceability and auditability without asserting clinical determinism or replacing clinician judgment.

The invention further supports dynamic application invocation, enabling seamless access to clinical applications, services, or tools in response to clinician intent without requiring separate authentication steps or manual navigation. This capability allows clinicians to transition between conversational interaction, informational responses, and application-driven workflows within a unified interaction model.

Unlike conventional clinical decision support tools that rely on static rules, predefined dashboards, or unguided conversational agents, the present invention enables real-time, interactive clinical reasoning conditioned on patient-specific data, temporal context, conversational state, and governance constraints. The system does not prescribe clinical action, but instead provides validated, context-aware informational outputs intended to assist clinicians while preserving clinician autonomy, accountability, and regulatory compliance.

The invention is not limited to any particular medical specialty, care setting, device topology, data source, interaction modality, or deployment architecture. Component boundaries, processing pathways, conversational handling mechanisms, and validation strategies may vary across embodiments while remaining within the scope of the disclosed system, provided that patient-related data is governed prior to reasoning and that artificial intelligence outputs are subject to validation prior to delivery.

Accordingly, the invention provides a governed, extensible, real-time clinical computing architecture that integrates medical data governance, artificial intelligence reasoning, supervisory orchestration, validation, and multimodal clinician interaction in a manner suitable for regulated healthcare environments, without requiring rigid workflows, fixed hardware configurations, or predetermined clinical conclusions.

All optional embodiments, including real-time conversational orchestration, multi-LLM execution, and standardized tool-calling interfaces, operate under the same governed medical data substrate and validation arbiter architecture.

BRIEF DESCRIPTION OF THE DRAWINGS

FIG. 1 illustrates an example system architecture showing interactions among a Medical Data Governance engine, artificial intelligence reasoning components, clinician-facing interfaces, intermediary data integration components, and external healthcare information systems, in accordance with one or more embodiments.

FIG. 2 illustrates an example interaction workflow between a Medical Data Governance engine and one or more large language models, showing preparation and delivery of governed context for artificial intelligence-based reasoning.

FIG. 3 illustrates an example workflow for processing a clinician-initiated request, including orchestration of multiple reasoning components, aggregation of intermediate outputs, validation, and delivery of an authorized output.

FIG. 4 illustrates an example modular collaboration architecture among artificial intelligence agents and large language models under orchestration and governance control, including real-time conversational interaction components that manage clinician dialogue, serialize conversational inputs, and coordinate governed processing and validated output delivery.

FIG. 5 illustrates an example arrangement of fast-thinking and slow-thinking artificial intelligence processing components operating under supervisory orchestration and validation control, including interaction with real-time conversational input handling to support low-latency response while preserving validation and governance enforcement.

FIG. 6 illustrates an example artificial intelligence execution architecture demonstrating modular processing, context segmentation, aggregation, and validation to improve computational efficiency.

FIG. 7 illustrates an example embodiment of insight delivery and task coordination, showing validation-controlled output distribution through clinician-facing applications and services.

FIG. 8 illustrates an example embodiment of contextual query handling, real-time conversational request serialization, and dynamic application invocation through a unified clinician-facing interaction model.

DETAILED DESCRIPTION OF THE INVENTION

Overview

In various embodiments, the disclosed subject matter relates to systems and methods for generating, under governance and authorization control, clinician-facing outputs derived from patient-related information obtained from heterogeneous clinical sources. The system may be implemented as an integrated software platform (the “insight platform”) that coordinates: (i) acquisition and governance of patient-related information by a Medical Data Governance (MDG) engine; (ii) preparation of governed context representations for downstream processing; (iii) orchestration of reasoning tasks across one or more large language models and/or specialized artificial intelligence agents; and (iv) validation-controlled delivery of authorized clinical outputs and/or invocation of clinical applications.

The embodiments described herein are not limited to any particular care setting, institution, deployment topology, or vendor ecosystem. The system may be deployed in local, on-premise, cloud-based, or hybrid configurations, and may interoperate with electronic healthcare information systems and external services through one or more application programming interfaces. The system is not limited to any particular messaging protocol, data model, or interface standard, and may operate with structured, semi-structured, and unstructured clinical information.

In some embodiments, the system supports clinician interaction by text, voice, or other interface modalities through one or more clinician-facing interfaces executing on one or more clinician devices. However, the invention does not require any particular audio hardware, full-duplex voice implementation, or specialized peripheral device. References to voice interaction are exemplary interaction modes and do not impose hardware requirements.

In various embodiments, clinician-facing interfaces may include handheld devices, head-worn devices, badge-like or pen-like wearable devices, pendant-style audio interfaces, room-mounted microphones, or other screenless or minimal-display devices configured to capture clinician speech and ambient conversational audio. These interfaces operate under the same authentication, governance, and validation controls described herein, and are treated as input channels to the governed conversational context rather than independent decision-making systems.

The illustrated hardware components are exemplary and non-limiting; equivalent logical, virtualized, or cloud-based data sources may be substituted without departing from the invention.

Medical Data Governance and Context Preparation

In various embodiments, patient-related information is received by a Medical Data Governance engine that serves as a governance authority configured to enforce access control, policy constraints, and contextual scope; perform validation, normalization, and time synchronization; maintain provenance, lineage, and audit metadata; and produce governed context representations suitable for downstream reasoning, analytics, or application use. The MDG engine may receive patient-related information from one or more medical devices and/or patient-associated sensing devices, and from one or more electronic healthcare information systems including, by way of example, electronic health record/electronic medical record systems, patient notes systems, radiology information systems, laboratory information systems, medication administration record systems, pharmacy information systems, population health management systems, admission-discharge-transfer systems, and other healthcare information systems.

In some embodiments, the MDG engine performs a context preparation process in which raw or derived clinical information is expanded, summarized, transformed, segmented, condensed, ranked, or annotated into representations suitable for artificial intelligence reasoning. Context preparation may be performed iteratively or conditionally based on query intent, governance policy, temporal scope, or feedback from downstream reasoning components. The output of context preparation may include one or more governed context representations and/or one or more context components, each being a task-specific portion of governed clinical context prepared for a particular reasoning model or specialized agent.

The governed context representations and context components may include structured data, unstructured narratives, abstractions, summaries, vectors, semantic indices, or composite representations, and are constrained to prevent unauthorized disclosure or ungoverned use. In some embodiments, governed context is maintained with multiple temporal scopes or resolutions (for example, fine-grained recent windows and coarser historical windows), and the MDG engine selects or produces appropriate context components responsive to the clinician request and applicable policy constraints. These examples are not limiting, and other temporal strategies may be used.

Reasoning and Orchestration Layer

In various embodiments, governed context is provided to a reasoning and orchestration layer that interprets clinician requests or system-initiated tasks, selects and sequences reasoning pathways, invokes one or more reasoning models and/or specialized artificial intelligence agents, and generates intermediate outputs and candidate clinical outputs while enforcing dependencies between reasoning, validation, and delivery stages.

A supervisory orchestration component may coordinate acquisition and routing of governed context; decomposition of clinician requests into subtasks; invocation and sequencing of reasoning components; aggregation of intermediate outputs; and enforcement of constraints and ordering between reasoning, validation, and delivery stages. The supervisory orchestration component may implement control logic, policies, state tracking, escalation rules, and feedback loops. The reasoning and orchestration layer may operate iteratively, conditionally, or in parallel, and may span heterogeneous compute environments.

In some embodiments, specialized artificial intelligence agents are invoked to perform focused analytical functions, such as analysis of recent data, short-term trends, longer-term patterns, statistical evaluation, or knowledge-based reasoning. Such agents may operate concurrently and may produce intermediate analytical outputs and/or intermediate functional outputs that are collected for aggregation. Intermediate outputs are explicitly non-final and are not authorized for clinical use.

In some embodiments, the system employs a combination of fast-thinking processing and slow-thinking processing. Fast-thinking processing may provide lower-latency analysis over constrained context and limited temporal scope. Slow-thinking processing may provide higher-assurance evaluation, including cross-checking, consistency analysis, and other assurance operations. These processing modes may be invoked conditionally based on the clinician request, detected uncertainty, governance policy, or other control signals.

Candidate Outputs, Aggregation, and Validation-Controlled Release

Reasoning components may generate candidate clinical outputs, which are preliminary synthesized results generated prior to authorization. Candidate clinical outputs are non-final and may be subject to validation, modification, combination, or rejection prior to delivery, presentation, storage, transmission, application invocation, or other downstream use.

In some embodiments, the system performs an aggregation process in which multiple intermediate outputs, agent responses, or model results are collected, combined, reconciled, and consolidated into a unified candidate output. Aggregation may include ranking, weighting, conflict detection, conflict resolution, summarization, normalization, or arbitration operations. Aggregation may occur within an aggregation and authorization stage, which conditionally routes the candidate output for validation, modification, or delivery based on authorization requirements, governance constraints, or control signals. A local orchestration and logic component may manage aggregation results, coordinate routing decisions, and mediate control signals between aggregation, validation, and delivery stages, without independently authorizing clinical output release.

A validation arbiter provides a validation-controlled release mechanism. The validation arbiter is configured to determine whether a candidate output is permitted to proceed to delivery, requires modification, or must be suppressed, based on one or more evaluation criteria including safety, governance policy, compliance constraints, or consistency requirements. The validation arbiter enforces non-bypassable release semantics by preventing delivery of outputs absent an affirmative authorization determination. In some embodiments, the validation arbiter may produce a validation signal representing approval, rejection, warning, or conditional authorization status.

In some embodiments, a check language model is optionally invoked as part of a validation, assurance, or safety workflow to independently assess candidate outputs for accuracy, truthfulness, internal consistency, bias, safety indicators, or compliance characteristics. The check language model provides analytical or corroborative input to support authorization decisions but does not itself authorize, block, modify, or release outputs for clinical use.

When a candidate clinical output satisfies applicable validation and authorization conditions, the system may generate an authorized clinical output. Authorization indicates that the output is permitted for presentation, transmission, storage, invocation, or downstream use under governance control, without limiting the format, destination, timing, modality, persistence, or degree of clinician reliance.

Delivery, Task Coordination, and Application Invocation

In various embodiments, authorized clinical outputs are delivered to one or more clinician-facing interfaces, which may include textual, graphical, voice-based, auditory, wearable, immersive, mixed-reality, or hybrid interfaces. Delivery may occur within one or more application contexts, each corresponding to a workflow, patient view, task, or application instance.

In some embodiments, the system supports a task coordination service that associates authorized outputs with executable tasks, workflow steps, reminders, notifications, or downstream service actions. Task coordination may integrate AI-derived insights into ongoing clinical, administrative, or operational processes without requiring predefined workflows or rigid task schemas.

In some embodiments, the system supports application invocation, in which a clinical application, service, or functional module is dynamically activated, launched, continued, embedded, orchestrated, or executed in response to a clinician request or system-determined condition. Application invocation may include session continuation, contextual binding, parameter passing, and seamless authentication mechanisms, and may result in application outputs presented to the clinician within an active application context. The invention does not require any particular single sign-on mechanism, identity provider, or integration protocol.

Clinician Oversight and Non-Determinism

The disclosed system provides safety-constrained decision support by generating and delivering outputs subject to governance controls, validation checks, and authorization conditions prior to presentation. The system does not require that outputs be treated as determinative clinical directives, and the embodiments described herein do not replace clinician judgment. In various embodiments, authorized clinical outputs may include contextual factors, limitations, uncertainties, or prompts for review, and may be structured to support clinical decision-making and workflow efficiency under applicable governance constraints.

In embodiments that employ continuous or ambient conversational capture, the system is further configured to expose explicit controls and indicators for such capture. For example, a clinician device, wearable conversational interface, or room-mounted audio interface may provide hardware or software mute controls, visible or audible status indicators, and audit-accessible logs of captured conversational segments. Institution-defined governance policies may restrict when conversational capture can occur, whether and how patient consent is obtained, how long captured audio or transcripts are retained, and which roles are permitted to access such information. These controls are enforced in coordination with the Medical Data Governance engine (150), the validation arbiter (220, 229), and associated security and privacy control components (541, 542, 558, 559, 560).

Conversational Interaction and Iterative Clinical Reasoning

In some embodiments, the system operates as an interactive clinician-facing assistant that supports iterative, natural-language dialogue regarding a patient and/or a clinical workflow. A clinician may submit a clinician request through a clinician-facing interface using typed input, voice input, or other interaction modalities. The request may be interpreted by a reasoning and orchestration layer to determine intent, temporal scope, and the types of governed context needed to address the request. The Medical Data Governance engine may then generate or select one or more governed context representations and/or context components responsive to the request and applicable governance policy constraints.

In these embodiments, the system may produce intermediate outputs during multi-stage reasoning and may update, refine, or supersede such intermediate outputs as additional governed context is retrieved or as additional clinician-provided information is received. Intermediate outputs are not authorized for clinical use and are not delivered as authorized clinical outputs unless and until validation is completed. Candidate clinical outputs generated by one or more large language models and/or specialized artificial intelligence agents may be aggregated and then provided to a validation arbiter. The validation arbiter determines whether a candidate clinical output is authorized for delivery, requires modification, or must be suppressed, and may optionally invoke a check language model to obtain corroborative analytical input regarding accuracy, internal consistency, safety indicators, or compliance characteristics.

The following scenarios illustrate non-limiting examples of how iterative clinician interaction may proceed. These examples are not intended to require any particular clinical practice, medication choice, or guideline, and do not replace clinician judgment.

Example Embodiment: Arrhythmia Management Under Hemodynamic Constraints

In one example embodiment, a clinician submits a request corresponding to a time-sensitive question regarding an arrhythmia in the presence of borderline hemodynamic status. The supervisory orchestration component may route the request to obtain governed context components including near-real-time physiological measurements, recent medication administration events, relevant historical response patterns, and constraints derived from policy or role-based access. One or more specialized artificial intelligence agents may be invoked to evaluate short-term trends, longer-term history, or statistical context, and may generate intermediate functional outputs for aggregation.

Based on the aggregated intermediate outputs, the reasoning layer may generate a candidate clinical output that highlights factors relevant to medication selection and monitoring (for example, current hemodynamic tolerance, timing of prior doses, or risk indicators detected in governed context). The validation arbiter may then authorize an output for delivery, authorize an output with warnings or conditional phrasing, or suppress the output if validation criteria are not met. In some embodiments, the system may generate follow-up prompts requesting missing information or suggesting verification steps, without instructing a clinician to take any specific action.

Example Embodiment: Neuromuscular Blockade Risk Screening

In another example embodiment, a clinician submits a request regarding suitability of a neuromuscular blocking agent. The system may retrieve governed context components including relevant diagnoses, historical findings, clinician-entered observations, prior procedures, and other contextual indicators available under governance constraints. The reasoning layer may generate a candidate clinical output describing potential risk indicators and alternatives framed as considerations rather than directives. The output may be iteratively refined based on additional clinician-provided details or newly ingested data, while remaining non-final until validation is completed.

In some embodiments, the system may identify potential contraindication signals or uncertainty conditions and may respond with a validated output that includes the basis for the flagged risk indicators (e.g., the specific governed context elements used), and may recommend that the clinician review or confirm particular data elements (e.g., labs, monitoring state, or historical notes) prior to relying on the output.

Example Embodiment: Incorporation of Clinician-Observed Findings and Verbal History In some embodiments, the system accepts clinician-provided observations and/or verbal history obtained at the point of care as part of a clinician request. Such observations may be provided via the clinician-facing interface as text, voice transcription, structured selections, or other input forms, and may be incorporated into governed context as permitted by governance policy. The system may then adapt reasoning scope and outputs based on the newly provided information, including identifying gaps in documentation, highlighting relevant risk categories, or producing structured considerations for peri-procedural planning. The system may further support generation of structured text suitable for documentation workflows, subject to governance constraints and validation-controlled release.

Workflow Integration and Task Coordination

In some embodiments, authorized clinical outputs may be associated with tasks using a task coordination service. For example, upon generating an authorized output that includes a recommended follow-up check, the system may propose creation of a reminder, a notification, or a workflow step within an application context. Task coordination may be configured to support continuity within and across clinician interactions without requiring predefined workflows or rigid task schemas. Any task-related action may be subject to policy constraints, role-based controls, and validation-controlled release semantics.

Exemplary Clinical Reasoning Workflows Under Governance Control

The following examples describe non-limiting embodiments in which the system supports clinician reasoning through governed data access, iterative interaction, and validation-controlled output delivery. These examples are provided for illustration only and are not intended to define clinical standards, mandate specific treatments, or replace clinician judgment. In each example, outputs generated by the system are subject to governance constraints, validation, and authorization prior to delivery and are intended to assist—not direct—clinical decision-making.

Across these and other embodiments, the system supports an interactive reasoning process in which governed context, modular analysis, and validation-controlled output delivery work together to assist clinicians in evaluating complex, time-sensitive situations. The system does not assert clinical determinism, mandate specific actions, or establish standards of care. Instead, it provides structured, explainable, and traceable assistance designed to augment clinician situational awareness while preserving clinician autonomy and responsibility.

Example Embodiment 1: Context-Aware Risk Identification for Neuromuscular Blockade In one exemplary embodiment, a clinician prepares for an anesthetic procedure and submits a clinician request regarding suitability of a neuromuscular blocking agent. The request may be submitted verbally or via text through a clinician-facing interface.

Upon receiving the request, the supervisory orchestration component interprets the request intent and determines that patient-specific historical data, clinician-entered observations, and recent procedural context are relevant. Governed context components may be retrieved from the Medical Data Governance engine, including documented diagnoses, imaging summaries, prior procedures, clinician-entered observations, and other contextual indicators permitted under governance policy.

One or more specialized artificial intelligence agents may analyze the governed context to identify potential risk indicators associated with neuromuscular blockade, including indicators derived from longitudinal history or clinician-observed findings not previously structured in an electronic record. These agents may generate intermediate functional outputs describing detected risk signals, uncertainty conditions, or gaps in available information.

The reasoning and orchestration layer aggregates these intermediate outputs into a candidate clinical output that describes considerations relevant to neuromuscular agent selection and peri-procedural monitoring. The candidate clinical output may include explanatory context indicating which governed data elements contributed to the identified considerations.

Prior to delivery, the candidate clinical output is evaluated by the validation arbiter. In some embodiments, the validation arbiter may invoke a check language model to assess internal consistency, safety indicators, and compliance characteristics. Upon successful validation, an authorized clinical output is delivered to the clinician-facing interface. The output may present considerations, cautions, and alternative planning factors without prescribing specific agents, doses, or actions.

The clinician may provide additional observations or clarification, resulting in further refinement of governed context and generation of updated candidate outputs. This iterative interaction may continue until the clinician concludes the interaction or no further refinement is requested.

Example Embodiment 2: Iterative Arrhythmia Management Reasoning with Real-Time Constraints In another exemplary embodiment, a clinician encounters an intraoperative or acute-care arrhythmia and submits a clinician request seeking assistance in evaluating management options under current physiological constraints.

The system retrieves governed context components corresponding to near-real-time physiological data, recent medication administration events, historical response patterns, and relevant procedural context. Specialized artificial intelligence agents may independently analyze short-term trends, longer-term historical patterns, and statistical context, generating intermediate functional outputs describing observed trends, risk indicators, and uncertainty conditions.

The reasoning and orchestration layer aggregates the intermediate outputs and generates a candidate clinical output describing considerations related to hemodynamic tolerance, timing of prior interventions, and monitoring implications. The output may optionally include follow-up prompts requesting confirmation of additional data elements or suggesting review of specific governed context components.

The candidate clinical output is evaluated by the validation arbiter prior to delivery. If authorized, the output is presented to the clinician in a format suitable for rapid review. The system may continue to update its internal reasoning state as new physiological data arrives, without automatically reissuing outputs unless prompted by the clinician or permitted by policy.

In some embodiments, the system may support optional task coordination, such as proposing reminders or monitoring prompts, subject to validation and clinician confirmation.

Example Embodiment 3: Integration of Bedside Observation and Undocumented History In a further exemplary embodiment, a clinician submits a clinician request based on bedside observation or verbal history obtained directly from a patient that is not present in structured electronic records.

The system accepts the clinician-provided information as part of the request and, where permitted, incorporates it into governed context with appropriate provenance and audit metadata. The reasoning layer evaluates the augmented governed context to identify potential implications for procedural planning, monitoring, or risk assessment.

Specialized artificial intelligence agents may generate intermediate outputs describing inferred risk categories, uncertainty conditions, or areas requiring additional verification. These outputs are aggregated into a candidate clinical output that highlights relevant considerations and explains the basis for those considerations using governed context elements.

After validation, an authorized clinical output may be delivered to the clinician. In some embodiments, the system may also generate structured text suitable for documentation workflows, subject to clinician review and confirmation.

This embodiment illustrates the system's ability to incorporate clinician-observed findings and verbal history into governance-controlled reasoning without requiring complete or preexisting documentation.

Real-Time Conversational Clinical Interaction, Input Serialization, and Governance-Preserving Orchestration In some embodiments, clinician interaction with the insight platform is performed through a real-time insight platform (205) that supports low-latency, turn-based interaction suitable for time-sensitive clinical workflows. The real-time conversational clinical interface—real-time insight platform (205) may operate using one or more conversational modalities, including voice input and optionally additional sensory or visual modalities, and may provide corresponding output modalities, including synthesized speech and/or visual rendering on a clinician-facing device. In such embodiments, the real-time insight platform (205) is coupled to, and cooperates with, a real-time conversational AI agent (206) that maintains an active conversational session with a clinician and manages conversational flow without bypassing governance or validation controls.

The real-time conversational AI agent (206) is configured to receive clinician utterances and other clinician interaction events, including interruptions, follow-on requests, clarifying answers, cancellations, and deferred actions, and to manage those events within a conversational session state. In operation, the real-time conversational AI agent (206) may perform session-level functions such as (i) detecting that a clinician input is incomplete or contextually insufficient for governed processing, (ii) generating a follow-on prompt requesting additional information, (iii) tracking multiple pending clinician requests within the same session, and (iv) prioritizing or deferring requests in response to interruption events or urgency signals. The real-time conversational AI agent (206) may also maintain modality continuity, such that a clinician request received via voice is responded to via voice unless an alternative modality is selected by the clinician or required by the interface. In some embodiments, the real-time conversational clinical interface-real-time insight platform (205) stores or logs a textual transcription of voice interaction for auditability, searchability, or later reference, while preserving patient-context associations and governance constraints.

To prevent uncontrolled propagation of continuous conversational streams into downstream clinical reasoning components, certain embodiments employ an input serialization and sequencing process (407). The input serialization and sequencing process (407) is configured to transform ongoing conversational interaction into a series of discrete, ordered user input units (207). Each user input unit (207) corresponds to a bounded request suitable for governed processing, and may include structured fields derived from clinician interaction, such as an identified patient context, an inferred intent classification, a temporal scope, a requested output class, and any clinician-supplied constraints. In some embodiments, the input serialization and sequencing process (407) assigns sequence identifiers, timestamps, and session linkage metadata to each user input unit (207) to preserve ordering and traceability.

Ambient conversational capture—refers to optional, governed acquisition of audio corresponding to clinician-patient or clinician-clinician conversations occurring in a patient care location, in which audio is transcribed into structured user input units and associated with an identified conversational session and governed context under institution-defined policies and controls. Ambient conversational capture does not itself constitute clinical decision-making authority and is subject to the same governance, consent, security, and validation constraints described for the real-time conversational clinical interface.

In embodiments employing process (407), clinician utterances, interruptions, and follow-on requests are not forwarded directly from the clinician-facing interface to the supervisory orchestration component (221) as a continuous stream. Instead, conversational interaction is mediated by the real-time conversational AI agent (206) and transformed by the input serialization and sequencing process (407) into one or more serialized user input units (207). The supervisory orchestration component (221) receives the serialized user input units (207) and initiates governed processing of each unit in accordance with the MDG engine (150), the reasoning layer, and the validation arbiter (220) described elsewhere herein. This arrangement enables controlled handling of conversational overlap, interruption, and deferred requests while preserving governance enforcement and auditability.

In some embodiments, the input serialization and sequencing process (407) further supports interruption-aware queue management. For example, when a clinician issues a new high-priority request while a prior request is in progress, process (407) may: (i) generate a new user input unit (207) assigned a higher priority, (ii) mark an earlier unit as deferred, paused, or awaiting continuation, and/or (iii) cause the supervisory orchestration component (221) to suspend, cancel, or reprioritize downstream reasoning tasks associated with the earlier unit, subject to governance constraints. Such suspension or cancellation may include halting generation of candidate clinical outputs not yet validated, discarding provisional intermediate outputs, or preventing further resource allocation to a superseded request. In some embodiments, the system maintains explicit state indicators for each unit, including pending, in-progress, deferred, cancelled, or completed, thereby supporting deterministic conversational behavior even when clinician interaction is non-linear.

For each serialized user input unit (207), the system generates one or more corresponding outputs that are handled as serialized outputs (208). A serialized output (208) may include an authorized response, an authorized partial response, a request for clarification, or an authorized action confirmation, provided that any clinical output content is subject to validation and authorization as described herein. In certain embodiments, the real-time conversational AI agent (206) and/or the real-time insight platform (205) controls delivery timing of serialized outputs (208) to preserve conversational coherence, such as by deferring delivery while the clinician is speaking, consolidating closely related outputs, or presenting an authorized clarification request before presenting substantive clinical content. In embodiments where an output includes a clarification prompt, the clarification prompt may be treated as an output that does not itself constitute a clinical recommendation and may be used to obtain additional clinician-provided context prior to generating candidate clinical outputs.

In some embodiments, the real-time conversational AI agent (206) performs "query readiness" assessment prior to emitting a user input unit (207) for governed processing. Query readiness assessment may include determining whether required context elements are present, such as patient identity, clinical episode, medication name, timeframe, or a specific clinical question type. When readiness criteria are not met, the real-time conversational AI agent (206) may generate an interactive prompt requesting one or more missing elements. Upon receiving the requested elements, the real-time conversational AI agent (206) may assemble a completed user input unit (207) and submit it for governed processing. This staged assembly reduces unnecessary downstream processing and mitigates the risk of producing outputs based on ambiguous or incomplete clinician requests.

The real-time conversational AI agent (206) and the input serialization and sequencing process (407) are configured such that they do not independently authorize, block, modify, or release clinical outputs for clinical use. In particular, outputs generated in response to serialized user input units (207) are treated as candidate clinical outputs unless and until evaluated by the validation arbiter (220) under governance constraints enforced by the MDG engine (150). The real-time conversational AI agent (206) may receive status signals indicating that a candidate output is pending validation, has been withheld, or has been authorized, and may use such status signals to manage conversational flow; however, the real-time conversational AI agent (206) does not bypass or override validation decisions.

In some embodiments, the real-time conversational AI agent (206) cooperates with application invocation or service execution logic to fulfill clinician requests that are not purely informational. For example, when a clinician requests that a particular clinical application view be opened or a configured service be invoked, the real-time conversational AI agent (206) may generate a structured command associated with a user input unit (207) and route the command through the supervisory orchestration component (221) to an application invocation pathway. In such embodiments, the system may distinguish between (i) governed informational outputs requiring validation prior to presentation and (ii) non-clinical control outputs or navigation actions that may be executed under access control and governance policy. Where an invoked action would result in presentation of clinical output content, the content remains subject to validation and authorization as described herein.

Accordingly, the embodiments described in this subsection provide a governance-preserving mechanism for real-time conversational clinician interaction by converting continuous conversation into discrete, ordered, and auditable units of governed processing. By combining the real-time conversational clinical interface-real-time insight platform (205), the real-time conversational AI agent (206), and the input serialization and sequencing process (407), the system supports rapid conversational workflows, interruption handling, deferred actions, and modality continuity, while ensuring that clinical outputs are not presented unless validated and authorized in accordance with the MDG engine (150) and validation arbiter (220).

Definitions

Medical device—refers to any clinical apparatus, instrument, system, or equipment that produces, measures, detects, derives, stores, processes, or conveys patient-related signals, measurements, waveforms, device states, alarms, or observations, and that makes such information available for downstream use through any wired, wireless, direct, indirect, native, adapted, or intermediary mechanism, without limitation as to regulatory classification, certification status, or physical form factor. (100, **100*b***)

Patient-associated sensing device—refers to any device, wearable, tracker, tag, or sensor associated with a patient that provides physiologic, biometric, behavioral, environmental, location, or contextual signals usable for patient-centric analytics, monitoring, or workflow association, whether continuous, periodic, event-driven, or opportunistic, and whether or not regulated as a medical device. (503)

Patient care location—refers to a physical, virtual, or logical point of care associated with a patient, including a bed, bay, room, operating area, recovery area, ward, station, assigned zone, or care context, and used as an organizing anchor for data association, context binding, routing, visualization, or workflow presentation. (500, 501)

Intermediary medical device integration component—refers to any component, module, service, adapter, gateway, edge function, virtualized instance, or intermediary arrangement that facilitates conveyance, transformation, or mediation of device-originated information toward downstream clinical services, including one or more of acquisition, protocol adaptation, buffering, relaying, time alignment, integrity checks, normalization, packaging, encryption, routing, filtering, or transport-enabling functions. The component may be implemented in hardware, software, firmware, or any combination thereof; may be deployed at the edge, centrally, or remotely; may be distributed across one or more locations; and may be omitted entirely in embodiments in which equivalent functionality is performed by other system components. (110, 120, 130, 700)

Intermediary coupling—refers to any mechanism, relationship, or means by which information, signals, data, or control messages are conveyed, exchanged, propagated, or made accessible between two or more components of the system, whether directly or indirectly. An intermediary coupling may be physical, logical, virtual, or abstract, and may include wired or wireless links, network paths, logical associations, software-mediated exchanges, message queues, streaming channels, buffered transfers, store-and-forward mechanisms, proxied or relayed communications, tunneled connections, shared memory, or any combination thereof. An intermediary coupling does not require a persistent connection, dedicated hardware, fixed topology, or specific transmission protocol, and is expressly not limited to any particular cable type, connector, interface standard, transport layer, or communication technology. (701)

Network infrastructure—refers to any communications substrate, transport fabric, or connectivity environment that conveys information between components of the platform and/or external systems, including local-area, wide-area, private, public, segmented, virtualized, overlay, VPN, wireless, wired, or hybrid networks. Network infrastructure may include multiple hops, intermediaries, gateways, security boundaries, or non-persistent transport abstractions, and is not limited to any specific networking protocol, topology, ownership domain, or administrative boundary. (180)

Remote management server—refers to any service, system, or functional component that may receive, aggregate, observe, relay, or interact with device-originated data or derived observations and that may additionally support one or more optional functions including provisioning, configuration, monitoring, diagnostics, logging, fleet management, lifecycle management, update coordination, or reliability services. A remote management server is not required in all embodiments, does not require centralized deployment, does not imply decision-making authority, and may be implemented as a distributed service, virtualized function, cloud-based service, on-premise system, or hybrid arrangement. (140)

Medical Data Governance engine—refers to a governance authority configured to receive patient-related information from heterogeneous sources; enforce access control, policy constraints, and contextual scope; perform validation, normalization, and time synchronization; maintain provenance, lineage, and audit metadata; structure, annotate, and contextualize data; and produce governed context representations suitable for downstream reasoning, analytics, or application use, while preventing unauthorized disclosure, inference, or ungoverned consumption of such data. (150)

Reasoning and orchestration layer—refers to one or more computational components that interpret clinician requests or system-initiated tasks, select and sequence reasoning pathways, obtain governed context from the Medical Data Governance engine, invoke one or more reasoning models or specialized agents, and generate candidate outputs and intermediate outputs while enforcing dependencies between reasoning, validation, and delivery stages. (210-218, 221, 222-228)

Validation arbiter—refers to a logical authorization authority configured to determine whether a candidate output is permitted to proceed to delivery, requires modification, or must be suppressed, based on one or more evaluation criteria including safety, governance policy, compliance constraints, or consistency requirements. The validation arbiter enforces non-bypassable release semantics by preventing delivery of outputs absent an affirmative authorization determination. The validation arbiter is not limited to any particular implementation and may rely on rules, heuristics, models, external signals, or combinations thereof. (220, 229)

Check language model—refers to a specialized artificial intelligence model that may be optionally invoked by a validation arbiter or by a local orchestration and logic component illustrated in the drawings and labeled as LLM CHECK (210) as part of a validation, assurance, or safety workflow to analytically assess candidate outputs generated by other reasoning components. The check language model provides evaluative or corroborative input to support authorization decisions but does not itself authorize, block, modify, or release outputs for clinical use.

Large language model—refers to any machine-learning-based language processing model capable of interpreting natural language inputs, generating natural language outputs, embedding or transforming language representations, performing reasoning or inference over structured or unstructured data, or supporting clinical, analytical, or operational tasks. Such models may be generative or non-generative, general-purpose or specialized, and may be deployed locally, on-premise, cloud-based, or in hybrid configurations. (210-219)

Supervisory orchestration component—refers to a coordinating control component configured to decompose clinician inputs or system-initiated tasks, manage acquisition and routing of governed context, invoke and sequence one or more reasoning models or specialized agents, aggregate intermediate outputs, and enforce dependencies, constraints, and ordering between reasoning, validation, and delivery stages. The supervisory orchestration component may implement control logic, policies, state tracking, escalation rules, and feedback loops, and ensures that validation and authorization requirements are satisfied prior to output delivery. (221, 221_a_, 221_b_, 221_c_)

Specialized artificial intelligence agent—refers to an AI-driven analytical component configured to perform a focused function, such as analysis of real-time data, short-term trends, long-term historical patterns, statistical evaluation, or knowledge-based reasoning. A specialized artificial intelligence agent may operate independently, concurrently, cooperatively, or conditionally under orchestration control, may consume governed context, and may produce intermediate analytical outputs without direct authority to authorize or deliver clinical outputs. (222-228)

Fast-thinking processing—refers to low-latency artificial intelligence-driven analysis optimized for rapid interpretation and immediate insight generation based on constrained context, limited temporal scope, or focused analytical objectives. Fast-thinking processing prioritizes responsiveness and timeliness while remaining subordinate to downstream validation, authorization, and governance controls prior to final clinical use. (222-228)

Slow-thinking processing—refers to deliberate, higher-assurance artificial intelligence-driven evaluation configured to perform deeper reasoning, cross-checking, consistency analysis, ethical review, and regulatory compliance verification. Slow-thinking processing functions as a gatekeeping or authorization-enabling mechanism and may be invoked conditionally or obligatorily prior to release of outputs for clinical use. (210, 220, 229)

Candidate clinical output—refers to any preliminary response, recommendation, interpretation, summary, alert, instruction, or synthesized result generated by one or more reasoning models or agents prior to authorization. Candidate clinical outputs are explicitly non-final, non-actionable, and subject to validation, modification, combination, or rejection prior to any delivery, presentation, or downstream use. (281-289, 421, 422, 431)

Authorized clinical output—refers to a candidate clinical output that has successfully passed validation and authorization checks and is permitted for presentation, transmission, storage, invocation, or downstream use under governance control. Authorization indicates compliance with applicable safety, governance, accuracy, and ethical constraints, without limiting the format, destination, timing, modality, persistence, or degree of clinician reliance. (441)

Clinician-facing interface—refers to any human-machine interface, software surface, or interaction layer through which a clinician may submit requests, receive outputs, review information, or interact with the system, including graphical, textual, voice-based, auditory, wearable, immersive, mixed-reality, or hybrid interfaces. A clinician-facing interface may execute locally or remotely, may be rendered on a clinician device or projected through another medium, and may support concurrent workflows, sessions, or application contexts. (240-244, 248, 251, 252)

Clinician request—refers to any query, command, instruction, prompt, selection, interaction, or implicit signal initiated by a clinician, whether expressed in natural language, structured form, voice input, gesture, image, interface interaction, or other modality. A clinician request may seek information, initiate reasoning, request validation, invoke an application, modify workflow state, or trigger a system action. (400, 401, 542)

Application invocation—refers to the dynamic activation, launch, continuation, embedding, orchestration, or background execution of a clinical application, service, or functional module in response to a clinician request or a system-determined condition. Application invocation may include session continuation, contextual binding, parameter passing, and seamless authentication without requiring separate manual login steps, and may result in application-generated outputs, interactive views, background processing, or downstream service actions. (254, 404)

Governed context—refers to a curated, policy-constrained representation of clinical data prepared under control of the Medical Data Governance engine, such representation being filtered, time-bounded, normalized, enriched, and scoped to ensure appropriateness for a specific reasoning task, request, or analytical objective. Governed context may include structured data, unstructured narratives, abstractions, summaries, vectors, or composite representations and is constrained to prevent unauthorized disclosure or misuse. (541, 266-269)

Contextual vector database—refers to a structured data representation, storage construct, or retrieval mechanism including vectorized, embedded, indexed, or semantically organized clinical information, prepared and maintained to provide efficient, relevant, and task-specific context to artificial intelligence models. A contextual vector database may be patient-specific, cohort-specific, time-bound, or purpose-specific and may be implemented as a dedicated database, embedded store, cache, or logical abstraction rather than a discrete physical database. (267, 269, 289)

Context preparation process—refers to one or more automated, semi-automated, or system-controlled procedures by which raw, derived, or structured clinical data is expanded, summarized, transformed, segmented, condensed, ranked, or annotated into representations suitable for artificial intelligence reasoning. Context preparation may occur iteratively, conditionally, or dynamically based on query intent, governance policy, temporal scope, or reasoning feedback. (262-264, 266)

Validation signal—refers to an explicit outcome, indicator, flag, or control artifact produced during validation that represents approval, rejection, required modification, warning, or conditional authorization status associated with a candidate output. Validation signals may be human-readable, machine-consumable, persistent or transient, and may influence downstream presentation, escalation, retry behavior, logging, auditability, or control flow. (229, 559)

Intermediate output—refers to any temporary, partial, streamed, provisional, or exploratory output generated during multi-stage reasoning, parallel processing, or iterative analysis. Intermediate outputs are not authorized for clinical use, are not intended for clinician reliance, and may be modified, replaced, aggregated, suppressed, or discarded prior to final validation and authorization. (422, 434, 439)

Aggregation process—refers to a synthesis operation that collects, combines, reconciles, or consolidates multiple intermediate outputs, agent responses, or model results into a unified candidate output while preserving contextual relevance, provenance, and governance constraints. Aggregation may include ranking, weighting, conflict detection, conflict resolution, summarization, normalization, or arbitration operations and may be iterative or conditional. (421, 431, 560)

Task coordination service—refers to a system capability that associates authorized outputs with executable tasks, workflow steps, reminders, notifications, or downstream service actions, enabling integration of AI-derived insights into ongoing clinical, administrative, or operational processes without requiring predefined workflows or rigid task schemas. (254)

Context-aware—refers to system behavior in which processing, reasoning, prioritization, or output generation is dynamically conditioned on patient-specific data, temporal scope, clinical state, workflow state, and governed contextual information prepared or constrained by a Medical Data Governance engine, such that identical inputs may yield different outputs under different validated contexts. (150, 261-269)

Safety-constrained decision support—refers to generation, conditioning, and delivery of system outputs that are subject to explicit governance controls, validation checks, and authorization conditions prior to presentation, such that outputs are traceable, auditable, context-bounded, and constrained by defined safety, regulatory, and policy rules, without asserting clinical determinism or replacing clinician judgment. (150, 220, 229)

Electronic healthcare information system—refers to any computerized system, service, repository, or application that stores, manages, processes, transmits, or exposes patient-related clinical, administrative, operational, or population-level healthcare information in structured, semi-structured, or unstructured form, and that may operate locally, remotely, on-premise, cloud-based, or in hybrid configurations, and may interoperate with other systems through standardized, proprietary, synchronous, or asynchronous interfaces. (170-179)

Electronic health record/electronic medical record system—refers to an electronic healthcare information system configured to maintain longitudinal patient medical records across encounters, including diagnoses, clinical notes, medications, allergies, procedures, problem lists, vital signs, orders, results, and encounter documentation, and to make such records available for clinical care, analytics, reporting, or decision support. (170)

Patient notes system—refers to any electronic system or repository that stores, manages, or exposes clinician-authored narrative content or structured documentation associated with a patient, including progress notes, operative notes, consult notes, discharge summaries, dictated reports, annotations, and free-text or semi-structured observations. (171)

Radiology information system—refers to an electronic healthcare information system configured to manage radiology-related workflows and data, including imaging orders, scheduling, procedure metadata, reports, result status, and associations to diagnostic imaging studies, whether or not image pixel data is stored, accessed, or managed within the same system. (172)

Laboratory information system—refers to an electronic healthcare information system configured to manage laboratory-related workflows and data, including test ordering, specimen identification and tracking, analytical results, reference ranges, abnormal flags, timestamps, and result status, and to associate such data with patient records and clinical workflows. (173)

Medication administration record system—refers to an electronic healthcare information system that records, tracks, and exposes medication administration events, including administered dose, timing, route, status, and responsible clinician, and that may represent scheduled, conditional, or as-needed medication delivery. (174)

Pharmacy information system—refers to an electronic healthcare information system configured to manage medication-related workflows, including medication ordering, verification, dispensing, inventory management, formulary enforcement, clinical checks such as drug-drug or drug-allergy interactions, and integration with prescribing or administration systems. (176)

Population health management system—refers to an electronic healthcare information system configured to aggregate, analyze, stratify, and manage health-related data across multiple patients or cohorts for purposes including risk stratification, quality measurement, outcomes analysis, care gap identification, and population-level clinical or operational insights. (177)

Admission-discharge-transfer system—refers to an electronic healthcare information system that records, manages, and exposes patient administrative and logistical events, including admission, discharge, transfer, location assignment, encounter status, and associated timestamps, and that provides authoritative signals for patient tracking, census management, workflow coordination, and context binding across clinical systems. (179)

Other healthcare information systems—refers to any electronic healthcare information systems not otherwise enumerated, including but not limited to clinical decision support systems, scheduling systems, billing or revenue cycle systems, registries, specialty-specific applications, external data feeds, research databases, or third-party clinical services that generate, store, or expose patient-related information usable under governance control. (178)

Clinician or clinician user—refers to a human healthcare professional authorized to participate in patient care, clinical decision-making, documentation, supervision, or oversight, including but not limited to physicians, nurses, advanced practice providers, technicians, pharmacists, or other licensed or credentialed clinical staff, who interacts with the system by submitting requests, reviewing outputs, or invoking applications. (255)

Clinician device—refers to any physical computing device used by a clinician to access the system, submit requests, receive outputs, or interact with applications, including smartphones, tablets, desktop computers, workstations, wearable devices, head-mounted displays, or other computing hardware capable of supporting one or more clinician-facing interfaces, whether institution-managed or personally provisioned. (400, 240-242)

insight platform—refers to an integrated software platform that coordinates clinician interaction, medical data governance, artificial intelligence reasoning, validation, and delivery of outputs, operating as an intermediary and control layer between clinician-facing devices and downstream clinical services, models, data sources, and applications. The insight platform may be deployed as a monolithic system, distributed services, or a hybrid arrangement. (200)

Real-time insight platform—refers to a governed clinical computing system configured to support real-time, conversational, and multimodal clinician interaction while preparing patient-related context under medical data governance controls, performing time-sensitive artificial intelligence-based reasoning, and delivering validated clinical informational outputs in temporal alignment with such interaction. The platform enforces non-bypassable validation and authorization prior to output delivery, supports interruption-aware and context-dependent workflows, and does not prescribe clinical actions or replace clinician judgment.

Large language model execution environment—refers to a computational environment in which one or more large language models are instantiated, executed, monitored, and invoked, including infrastructure providing compute, memory, storage, runtime isolation, and lifecycle management, and which may be local, on-premise, cloud-based, edge-based, or hybrid. (201)

Medical Data Governance server API environment—refers to a server-side execution environment that hosts Medical Data Governance services and exposes governed data, policies, and control functions through one or more application programming interfaces, enabling downstream components to request, retrieve, or operate on governed context under enforced policy constraints. (202)

Medical Data Governance interface boundary—refers to a logical, technical, or policy-enforced boundary separating the Medical Data Governance engine from downstream reasoning, orchestration, or application components, across which requests and governed data are exchanged exclusively through defined interfaces, thereby preventing unauthorized or ungoverned access. (203)

Application programming interface—refers to a defined software interface through which components exchange data, invoke functions, or request services, including synchronous or asynchronous interfaces, event-driven interfaces, or message-based interfaces, and including standardized, proprietary, or hybrid protocols, without limitation to any specific implementation technology or data model. (544)

Candidate response—refers to a candidate clinical output generated during reasoning, aggregation, or synthesis stages prior to authorization, and is synonymous with candidate clinical output for purposes of interpretation, validation, and claim construction. (281-289, 421, 431)

Context component—refers to a discrete, task-specific portion of governed clinical context prepared by the Medical Data Governance engine and supplied to a particular reasoning model or specialized agent. A context component is partial, constrained, and tailored to a specific analytical purpose, temporal scope, or reasoning task, and may represent one of multiple concurrent context slices derived from a broader governed context. (541, 551)

Intermediate functional output—refers to an output produced by an individual reasoning model or specialized agent during distributed, staged, or parallel processing, representing a partial analytical result that is collected for subsequent aggregation or validation and is not authorized for clinical use. Intermediate functional outputs may be transient, replaceable, or superseded during processing. (555)

Aggregation and authorization stage—refers to a processing stage in which multiple intermediate outputs are synthesized, reconciled, or consolidated into a unified candidate output and conditionally routed for validation, modification, or delivery based on authorization requirements, governance constraints, or control signals. (560)

Local orchestration and logic component—refers to a control component responsible for managing aggregation results, coordinating routing of candidate outputs to validation or delivery paths, and mediating control signals between aggregation, validation, and output stages, without independently authorizing, blocking, modifying, or releasing clinical outputs.

In the illustrated embodiments, this functionality is implemented by, or incorporated within, the supervisory orchestration component (221), although other implementations may distribute these functions across one or more control components.

Displayed output answer—refers to a validated and authorized clinical output rendered directly to a clinician-facing interface as a response to a clinician request, without invoking a separate clinical application, and presented in a format suitable for immediate clinical review or action. (253)

Application output—refers to content, views, data presentations, or functional responses generated by an invoked clinical application or service and presented to the clinician within an active application context, which may include interactive elements, workflows, or task-driven interfaces. (254)

Application context—refers to a distinct interactive workspace, session, or logical container within a clinician-facing interface corresponding to a specific workflow, patient view, task, or application instance, and capable of operating concurrently with other application contexts without loss of session continuity. (531-534)

Interaction elements/history blocks—refers to interface components that enable clinician interaction, input submission, response display, and retention of historical queries, outputs, or application interactions, supporting continuity, review, navigation, or audit of prior system activity. (535)

Input serialization and sequencing process—refers to a control process that converts continuous or overlapping conversational interaction into a sequence of discrete, ordered user input units, preserving conversational ordering, interruption handling, deferred requests, and prioritization, while ensuring that each input unit is independently subject to governance, orchestration, reasoning, and validation controls, and application invocations are processed in a governed, serialized manner prior to submission to regulated reasoning and validation workflows.

Real-time conversational interaction component—refers to a system component configured to manage live, interactive communication with a clinician using time-sensitive modalities such as voice and/or other multimodal inputs, maintain conversational state across multiple turns, handle interruptions and prioritization, and transform conversational interaction into structured user input units for governed processing by downstream orchestration, reasoning, and validation components. The real-time conversational interaction component does not independently generate, authorize, modify, or release clinical outputs.

Conversational session—refers to a temporally bounded interactive exchange between a clinician and the system in which multiple conversational inputs, interruptions, follow-on requests, and system responses occur under a shared conversational context and session state.

Real-time conversational clinical interface—refers to a clinician-facing interface modality through which real-time conversational interaction is conducted, including voice-based interaction and optional multimodal outputs, and through which serialized conversational outputs are presented following validation and authorization.

Structured user input unit—refers to a discrete, machine-interpretable representation of clinician intent derived from conversational interaction, suitable for governed processing by the supervisory orchestration component and downstream reasoning and validation components.

Serialized output unit—refers to a candidate or authorized clinical output that is temporally associated with a corresponding structured user input unit and delivered to the clinician in an order consistent with serialized conversational processing.

Conversational state—refers to transient information maintained during a conversational session that reflects pending requests, interrupted inputs, deferred actions, prioritization conditions, and response sequencing, without constituting clinical decision-making authority.

Multimodal conversational interaction—refers to conversational interaction that incorporates more than one modality, including but not limited to voice, visual rendering, gesture, or spatial interface output, within a unified conversational session.

Model Context Protocol (MCP)—refers to an interface mechanism by which governed context, structured data representations, or policy-constrained information is made available to one or more artificial intelligence models in a controlled, auditable, and non-bypassable manner.

Conversational turn—refers to a single unit of clinician input or system response within a conversational session, which may correspond to one or more structured user input units or serialized output units.

Ambient conversational capture—refers to optional, governed acquisition of audio corresponding to clinician-patient or clinician-clinician conversations occurring in a patient care location, in which audio is transcribed into structured user input units and associated with an identified conversational session and governed context under institution-defined policies and controls. Ambient conversational capture does not itself constitute clinical decision-making authority and is subject to the same governance, consent, security, and validation constraints described for the real-time conversational clinical interface.

DETAILED DESCRIPTION OF THE FIGURES

FIG. 1 System Architecture Overview illustrates an example system architecture of an insight platform, depicting interactions among a Medical Data Governance (MDG) engine (150), a reasoning and orchestration layer comprising one or more large language models (210-218), modular artificial intelligence agents (222-228), a supervisory orchestration component (221), a validation arbiter (220), clinician-facing interaction interfaces (240-244, 248, 251, 252), one or more intermediary medical device integration components (110, 120, 130, 700), and external healthcare information systems (170-179).

In the illustrated embodiment, patient-related clinical data may originate from one or more medical devices (100, 100*b*) and/or patient-associated sensing devices (503) operating at or near a patient care location (500, 501). The devices may produce real-time physiological measurements, waveforms, device status, alarms, or other clinical signals. Such device-originated data may be conveyed, directly or indirectly, through one or more intermediary acquisition, adaptation, or transport components represented in FIG. 1 by example elements (110, 120, 130, 700) and corresponding couplings (701). The intermediary components may perform one or more of signal acquisition, protocol adaptation, buffering, relaying, time alignment, integrity checks, normalization, packaging, encryption, routing, or other functions that facilitate conveying device-originated information to downstream clinical services. The particular partitioning of functions among intermediary components, and the physical form or deployment location of such components, may vary across embodiments.

Device-originated data and/or derived observations may be communicated via one or more network infrastructures (180) to a remote management server (RMS) (140). In some embodiments, the RMS (140) aggregates incoming device data, associates such data with patient identifiers and contextual metadata (143), and forwards the aggregated information to the MDG engine (150). The RMS (140) may additionally support configuration, provisioning, monitoring, diagnostics, or logging for one or more upstream and downstream components, although such functions are optional and may be implemented by other services in alternative embodiments.

The MDG engine (150) operates as a central governance authority configured to receive, validate, time-synchronize, structure, contextualize, and govern patient-related data prior to use by reasoning components. As illustrated, the MDG engine (150) may integrate data from electronic health record or electronic medical record systems (EHR/EMR) (170), patient notes (PN) (171), radiology information systems (RIS) (172), laboratory information systems (LIS) (173), medication administration records (MAR) (174), pharmacy information systems (PIS) (176), population health management systems (PHM) (177), admission-discharge-transfer systems (ADT) (179), and other healthcare information systems or data sources (178). The MDG engine (150) enforces governance policies, access controls, provenance constraints, and context constraints on patient data and may produce governed context representations for downstream processing.

Governed and context-constrained data from the MDG engine (150) is supplied to a reasoning layer comprising one or more large language models (210-218) and modular artificial intelligence agents (222-228). The supervisory orchestration component (221) coordinates interactions among the MDG engine (150), the large language models, and the modular agents, and is configured to receive clinician-initiated requests and/or system-generated tasks, determine applicable temporal scopes and clinical contexts, and route governed data to selected reasoning components.

In some embodiments, when clinician interaction is performed through a real-time conversational clinical interface-real-time insight platform (205) via a real-time conversational AI agent (206), clinician utterances, interruptions, and follow-on requests are not forwarded directly to the supervisory orchestration component (221). Instead, such interactions are first processed by an input serialization and sequencing process (407), which transforms continuous conversational input into a series of discrete, ordered user input units (207). Each serialized user input unit is processed independently under governance control, and corresponding system responses are generated as serialized outputs (208). This arrangement ensures that conversational modality, ordering, interruption handling, and deferred requests are preserved without permitting bypass of governance, orchestration, or validation mechanisms.

As illustrated, the modular agents (222-228) may be configured for specialized analytical functions that include, by way of example, near-real-time analysis (222), short-term analysis (223), longer-term analysis (224), historical patient analysis (225), demographic or statistical analysis (226, 227), and knowledge-base-driven reasoning (228). The agents may operate independently and in parallel under orchestration control while consuming governed data and producing intermediate outputs or candidate clinical outputs.

Candidate outputs generated by the large language models (210-218) and/or modular agents (222-228) are provided to a validation arbiter (220) that evaluates candidate outputs for clinical accuracy, internal consistency, safety, and compliance with governance rules enforced by the MDG engine (150). In some embodiments, the validation arbiter (220) may invoke a checking large language model, labeled LLM CHECK (210) as part of the evaluation. Outputs are withheld from clinician presentation until explicitly authorized.

In addition to the checking language model invoked by the validation arbiter, in some embodiments a large language model labeled LLM M (211) is invoked by a supervisory or aggregation component, illustrated as (221), as part of a primary reasoning or synthesis workflow. The LLM M (211) is configured to generate, refine, or transform candidate clinical outputs based on governed context supplied by the MDG engine (150) and intermediate outputs produced by modular agents (222-228). Outputs produced by LLM M (211) are treated as candidate clinical outputs and are routed to the validation arbiter (220) for evaluation prior to any presentation to a clinician. The invocation of LLM M (211) does not confer authorization authority and does not bypass validation, and no output generated by LLM M (211) is presented to a clinician unless explicitly authorized by the validation arbiter.

Authorized outputs are delivered to one or more clinician-facing interaction interfaces, including a smartphone interface (240), a desktop or tablet interface (241), wearable or head-mounted interfaces (242, 248, 251, 252), and voice or audio-based interaction devices (243, 244). The interfaces may present governed, validated clinical insights, alerts, or recommendations while maintaining association with the originating patient context.

The architecture illustrated in FIG. 1 represents one example implementation. Component boundaries, deployment locations, intermediary device integration mechanisms, network arrangements, and data flow paths may vary while remaining within the scope of the disclosed system, provided that patient data is governed by the MDG engine (150) and that artificial intelligence outputs are subject to validation prior to clinician presentation.

FIG. 2: LLM-MDG Interaction Workflow illustrates an example interaction workflow between the Medical Data Governance (MDG) engine (150) and one or more large language models (LLMs) (210-219), showing how clinical data is iteratively expanded, condensed, and prioritized to generate governed, patient-specific contextual inputs for AI-driven clinical reasoning. The illustrated workflow enables dynamic refinement of medical data under governance constraints, ensuring that clinical insights generated by AI models are contextualized, relevant, and suitable for real-time clinical decision support.

In the illustrated embodiment, the MDG engine (150) receives real-time and historical patient-related data from multiple heterogeneous sources, including a remote management server (RMS) (140) aggregating bedside medical device data, electronic health record systems (EHR/EMR) (170) and associated clinical subsystems such as patient notes (PN) (171), radiology information systems (RIS) (172), laboratory information systems (LIS) (173), and medication administration records (MAR) (174), as well as data originating from wearable devices or third-party medical systems. Incoming data is time-synchronized, validated, and structured into one or more timestamped patient datasets (261) associated with a specific clinical episode.

The MDG engine (150) processes the structured patient datasets through one or more governance-controlled transformation stages that expand and contextualize the data. In some embodiments, raw numerical values and time-series measurements are translated into descriptive representations reflecting known clinical conditions, statistical properties, and observed trends (262-263). For example, sequences of physiological measurements may be transformed into descriptive phrases indicating stability, variability, deviation from baseline, or clinically significant patterns, rather than being provided as unprocessed numeric streams.

Based on the expanded and contextualized representations, the MDG engine generates one or more condensed, LLM-optimized context representations (266-269). These representations may include vectorized medical language constructs, statistical summaries, or prioritized subsets of patient data selected according to temporal relevance, clinical significance, or governance policies. By condensing and prioritizing information at the MDG layer, the system limits the data exposed to downstream AI models to information that is both clinically relevant and contextually appropriate.

The LLM-optimized context representations are provided to one or more large language models (210-219) for query-driven analysis. In some embodiments, a supervisory orchestration component determines which LLMs or reasoning modes are invoked based on the nature of a clinician query and the available contextual data. Different LLMs may be employed to analyze real-time data, short-term trends, long-term historical patterns, or population-level statistics, and the interaction between the MDG engine and the LLMs may be iterative, with updated contextual constraints generated in response to intermediate reasoning results.

Outputs generated by the LLMs are structured as candidate clinical outputs (281-289), which may include summaries, interpretations, or recommendations derived from the governed context supplied by the MDG engine. These candidate outputs are subsequently subject to downstream validation and authorization processes, as described with respect to other figures, prior to presentation to clinician-facing interfaces. Clinicians receive authorized AI-generated insights via one or more user interfaces, including web applications, mobile dashboards, or wearable devices.

The LLM-MDG interaction workflow illustrated in FIG. 2 enables adaptive and context-aware clinical reasoning by continuously refining how patient data is expanded, condensed, and prioritized under governance constraints. This approach supports accurate, timely, and compliant clinical insights while maintaining strict control over data exposure and AI reasoning inputs.

FIG. 3: Workflow of Query Processing illustrates an example workflow for processing a clinician's query within the insight platform, showing how a user-initiated request is orchestrated across multiple artificial intelligence models, evaluated under governance constraints, and returned as an actionable clinical output. The illustrated workflow demonstrates how parallel reasoning, intermediate streaming outputs, and final validation are combined to deliver context-aware and compliant clinical insights.

In the illustrated embodiment, the workflow begins when a clinician submits a query (401) through a supported interface, such as a web-based dashboard, mobile device, wearable device, or voice-based interface. The input query is received by a supervisory orchestration component, which processes the query using an initial large language model to interpret intent, extract relevant clinical parameters, and generate one or more structured sub-queries (402-403). In some cases, the supervisory orchestration component may request additional context or clarification before proceeding.

Based on the structured query, the supervisory orchestration component selectively invokes none, one, or multiple specialized large language models operating in parallel (412-419). These models may analyze different temporal scopes or data dimensions, such as near-real-time patient data, short-term trends, longer-term historical records, or demographic context. Patient-specific data used by the models is retrieved through the Medical Data Governance (MDG) engine, ensuring that only governed, context-constrained information is supplied to the reasoning layer.

As illustrated, the system may generate intermediate or temporary outputs in a streaming manner while parallel model processing is ongoing (421-422, 434). These temporary outputs are non-final and are not confirmed for clinical use until downstream validation is completed. Outputs produced by the parallel LLMs are collected and consolidated into one or more candidate responses (421), which are further processed by an aggregation model to synthesize a coherent clinical answer (431).

Prior to final delivery, candidate clinical outputs are subjected to validation and consistency checking. One or more models may be invoked to perform cross-checking, truthfulness assessment, or internal consistency evaluation of the synthesized response (433). The candidate output is then evaluated by a validation arbiter, which determines whether the response satisfies applicable clinical, ethical, safety, and governance constraints. If potential issues or red flags are detected (435), the system may modify the response, generate warnings, or require additional processing before release.

Upon successful validation and authorization under a final authorization control path, the system confirms the clinical output and presents the finalized response to the clinician through the selected interface (441-442). In some cases, the output may include warnings, annotations, or follow-up prompts to support informed clinical decision-making. The query processing session and associated authorization outcomes may be selectively logged for auditability and traceability.

FIG. 3 illustrates a flexible, governance-aware query processing workflow in which clinician inputs are dynamically orchestrated across multiple AI models, validated under strict controls, and delivered as reliable, context-sensitive clinical insights.

FIG. 4: Modular AI Agent Collaboration illustrates an example embodiment of a modular artificial intelligence agent collaboration architecture implemented within the insight platform, depicting how clinician-initiated interactions are mediated, serialized, orchestrated, reasoned upon, validated, and delivered under medical data governance control to produce clinically actionable outputs. In the illustrated embodiment, the architecture spans an insight platform interaction environment (200), a large language model execution environment (201) that may be local, on-premise, cloud-hosted, or hybrid, and a Medical Data Governance server API or recently adopted Model Context Protocol (MCP) interface environment (202).

A clinician user (255) interacts with the system through one or more clinician-facing interfaces, including a smartphone web-based clinical dashboard (240), a desktop or tablet clinical application interface (241), a wearable clinical interface (242), a voice-enabled interaction device (243), a bone-conduction or audio output device (244), an augmented or mixed-reality display interface (248), a wearable computing device (251), or a head-mounted visual interface (252). These interfaces collectively form an insight platform real-time conversational clinical interface-real-time insight platform (205) capable of supporting multimodal interaction, including voice, text, gesture, or mixed-reality input and output.

In the illustrated embodiment, clinician interaction is first mediated by a real-time conversational artificial intelligence agent (206). The real-time conversational AI agent (206) is configured to manage live, bidirectional interaction with the clinician, including handling natural-language dialogue, turn-taking, interruptions, follow-up requests, deferred actions, reminders, and parallel conversational intents. The conversational AI agent (206) operates as a modality-aware interaction manager and does not itself perform regulated clinical reasoning or authorize clinical outputs.

Clinician utterances, gestures, or textual entries are received as serialized user input events (401), each corresponding to a distinct user input instance (USER INPUT n) (207). The conversational AI agent (206) maintains conversational state across successive USER INPUT n events, resolves ambiguities, requests clarification when needed, and ensures that each serialized input is sufficiently complete and semantically well-formed prior to submission for regulated processing. When a given USER INPUT n (207) is determined to require governed reasoning, the conversational AI agent (206) transforms and forwards the serialized input (401) to a supervisory orchestration component (221), preserving ordering, contextual continuity, and isolation between concurrent or successive requests. The conversational AI agent (206) may concurrently manage additional conversational tasks—such as reminders, interruptions, or queued follow-up requests—without blocking regulated processing.

The supervisory orchestration component (221), operating within the large language model execution environment (201), functions as the primary coordinating entity for regulated reasoning workflows. Upon receiving a serialized user input (401), the supervisory orchestration component (221) interprets the request, extracts relevant clinical parameters, determines applicable temporal scopes, and selects appropriate reasoning pathways. The supervisory orchestration component (221) communicates with a Medical Data Governance engine (150) via an MDG-facing orchestration interface (221*a*) across an MDG interface boundary (203). The Medical Data Governance engine (150), operating within the MDG server API or MCP environment (202), supplies governed, time-synchronized, and context-constrained patient data while enforcing access controls, provenance requirements, and governance policies.

Based on the interpreted request, the supervisory orchestration component (221) selectively invokes none, one, or multiple specialized artificial intelligence agents (222-228) in parallel. These agents include, by way of example, a real-time clinical agent (222) operating over a short temporal window, a short-term clinical agent (223) operating over approximately one hour, a mid-range clinical agent (224) operating over approximately twenty-four hours, a historical patient monitoring agent (225), short-term and historical demographic statistical agents (226, 227), and a knowledge-base agent (228). Each agent consumes governed data supplied by the Medical Data Governance engine (150) and produces intermediate analytical outputs.

In addition to invoking specialized agents, the supervisory orchestration component (221) may invoke one or more large language models (210-219), including primary reasoning models, aggregation or synthesis models, and containerized model groups. In some embodiments, a large language model labeled LLM M (211) is invoked by the supervisory orchestration component (221) as part of a primary reasoning or synthesis workflow to generate, refine, or transform candidate clinical outputs based on governed context and intermediate agent outputs. Outputs produced during this stage may include intermediate application outputs (404) or temporary outputs (432), which are explicitly non-final, non-authorized, and withheld from clinician presentation.

Intermediate outputs and synthesized candidate clinical outputs produced by the modular agents (222-228) and the large language models (210-219), including outputs generated by LLM M (211), are routed to a validation arbiter (220) via an authorization and validation control path (229). The validation arbiter (220) operates as a non-bypassable authorization authority responsible for evaluating candidate clinical outputs for clinical validity, internal consistency, patient safety, regulatory compliance, and adherence to governance constraints enforced by the Medical Data Governance engine (150). As part of this evaluation, the validation arbiter (220) may invoke a checking large language model, labeled LLM CHECK (210), to provide independent analytical assessment. Neither the primary reasoning models nor the checking model possess authority to authorize output delivery.

Candidate outputs remain withheld until explicitly authorized by the validation arbiter (220). Outputs that fail validation may be modified, rejected, or returned to the supervisory orchestration component (221) via a validation-facing interface (221*b*), without permitting bypass of the validation decision.

Upon successful authorization, the validation arbiter (220) confirms a final authorized output (441). The authorized output is returned through the supervisory orchestration component (221) and forwarded to the real-time conversational AI agent (206). The conversational AI agent (206) delivers the authorized output to the clinician in the same modality as the originating USER INPUT n (207), such as spoken audio, textual display, mixed-reality visualization, or application invocation. In embodiments involving voice interaction, the conversational AI agent (206) may generate spoken output while concurrently logging a textual transcription for auditability, traceability, and later review. Completion of a regulated interaction may be recorded as a session completion event (442).

The architecture illustrated in FIG. 4 represents one example embodiment. The allocation of conversational mediation, orchestration logic, reasoning components, validation processes, execution environments, interface modalities, and serialization mechanisms may vary across implementations while remaining within the scope of the disclosed system, provided that clinician interaction is mediated through serialized inputs, patient data is governed by the Medical Data Governance engine (150), and no artificial intelligence output is presented to a clinician without prior validation and authorization.

FIG. 5: Real Time, Fast and Slow Thinking Component Operations illustrates an example embodiment of a dual-layer artificial intelligence processing architecture implemented within the insight platform, depicting coordinated operation between fast-thinking artificial intelligence components, slow-thinking artificial intelligence components, and a real-time conversational interaction layer to balance immediate clinical responsiveness with deeper contextual reasoning, validation, and governance enforcement.

In the illustrated embodiment, a real-time conversational artificial intelligence agent (206) operates as an interaction-facing mediation layer between a clinician user and the regulated artificial intelligence processing architecture. The conversational AI agent (206) is configured to manage live, bidirectional clinician interaction, including voice-based real-time interaction and, optionally, additional multimodal interaction modalities, turn-taking, interruption handling, clarification requests, deferred actions, and queued follow-up requests. The conversational AI agent (206) serializes clinician interactions into discrete user input instances and forwards regulated requests to downstream processing only after ensuring that each request is sufficiently complete and semantically well-formed. The conversational AI agent (206) does not independently perform regulated clinical reasoning and does not authorize clinical outputs.

A supervisory orchestration component (221) operates as a central coordination layer positioned between the real-time conversational AI agent (206), a fast-thinking processing layer, and a slow-thinking processing layer. The supervisory orchestration component (221) is configured to receive serialized, regulated user inputs from the conversational AI agent (206), along with structured clinical tasks or intermediate reasoning outputs, and to distribute processing workloads across multiple specialized artificial intelligence agents according to temporal urgency, clinical context, and governance constraints.

The fast-thinking processing layer comprises a plurality of specialized fast-thinking AI agents (222-228) configured to operate with low latency and to provide immediate or near-immediate analytical outputs. These agents include, by way of example, a real-time patient analysis agent (222) configured to analyze governed patient data associated with a short temporal window, a short-term patient analysis agent (223) configured to evaluate patient data over an intermediate temporal window of approximately one hour, a twenty-four-hour patient analysis agent (224) configured to analyze daily clinical trends, a historical patient analysis agent (225) configured to analyze longitudinal patient history, a short-term demographic statistical agent (226), a historical demographic statistical agent (227), and a knowledge-base artificial intelligence agent (228) configured to incorporate curated medical knowledge and reference datasets. Each fast-thinking agent operates independently and in parallel, receiving governed patient data supplied via the supervisory orchestration component (221) and producing time-sensitive analytical outputs suitable for rapid clinical awareness.

Outputs generated by the fast-thinking AI agents (222-228) are aggregated and synthesized by the supervisory orchestration component (221) into preliminary or intermediate candidate clinical outputs. In some embodiments, such intermediate outputs may be provisionally routed back to the real-time conversational AI agent (206) as non-authorized, temporary responses for conversational continuity, such as acknowledgments, progress indicators, or requests for additional clarification, while remaining withheld from clinical decision use and subject to downstream validation.

The slow-thinking processing layer comprises one or more artificial intelligence components configured for deeper contextual reasoning, cross-agent reconciliation, validation, and governance enforcement. In the illustrated embodiment, the slow-thinking layer includes a validation arbiter (220) and a check large language model (210). The validation arbiter (220) operates as an authoritative decision-making component responsible for assessing synthesized candidate outputs against regulatory requirements, ethical constraints, patient safety policies, and governance rules enforced by the Medical Data Governance engine (150). The check large language model (210) may be optionally invoked by the validation arbiter (220) to independently evaluate clinical accuracy, truthfulness, internal consistency, bias indicators, or safety-related characteristics of candidate outputs.

Interaction between the fast-thinking and slow-thinking layers is mediated by the supervisory orchestration component (221) through an internal control loop (229). When intermediate outputs produced by the fast-thinking layer require deeper evaluation, confirmation, or conflict resolution, the supervisory orchestration component (221) escalates such outputs to the slow-thinking layer. The validation arbiter (220), optionally invoking the check large language model (210), determines whether a candidate output is authorized for clinical use, requires modification, or must be rejected. When authorization is denied or modification is required, feedback is returned to the supervisory orchestration component (221) without permitting bypass of the validation decision.

Upon explicit authorization by the validation arbiter (220), a final authorized clinical output is returned through the supervisory orchestration component (221) to the real-time conversational AI agent (206). The conversational AI agent (206) then delivers the authorized output to the clinician in the same modality as the originating interaction, such as spoken audio, textual display, or mixed-reality visualization, while preserving conversational continuity. In voice-based embodiments, the conversational AI agent (206)

may generate audible output while concurrently logging a textual transcript for traceability and audit purposes.

In some embodiments, the real-time conversational AI agent (206) operates outside the fast-thinking and slow-thinking analytical layers illustrated in FIG. 5. The conversational AI agent (206) is not configured to perform clinical reasoning, validation, or governance enforcement. Instead, it manages clinician interaction flow, modality handling, interruption control, and serialization of conversational input through an input sequencing process (407). Serialized conversational inputs are then submitted to the supervisory orchestration component (221) for allocation to fast-thinking agents (222-228) and, where required, escalation to slow-thinking validation processes (220, 210). This separation ensures that real-time conversational responsiveness does not compromise analytical rigor or governance enforcement.

The dashed boundary illustrated between the fast-thinking and slow-thinking layers represents a logical separation between rapid analytical processing and deliberate validation processing, while permitting controlled bidirectional communication under orchestration control. The inclusion of the real-time conversational AI agent (206) enables immediate clinician interaction and responsiveness without compromising governance, safety, or authorization requirements.

Through this dual-layer processing architecture with real-time conversational mediation, FIG. 5 illustrates how the insight platform enables high-speed clinical analysis and interactive clinician engagement while maintaining rigorous oversight, contextual reasoning, and regulatory compliance through non-bypassable validation and governance mechanisms.

FIG. 6: Energy Efficiency and Cost Optimization illustrates an example embodiment of an energy-efficient and cost-optimized artificial intelligence processing architecture implemented within the insight platform, demonstrating how Medical Data Governance-driven context preparation, modular large language model execution, and selective task allocation reduce computational load, energy consumption, and operational cost while maintaining clinical accuracy and governance.

In the upper portion of FIG. 6, a conventional large language model execution pattern is illustrated, in which a single large language model instance operating on a single GPU or CPU computational unit is provided with a massive patient context vector containing heterogeneous data aggregated from hospital information systems, electronic medical records, historical patient data, and real-time physiological data. In such a configuration, a clinician query is processed against an extremely large vector space, resulting in high memory utilization, elevated GPU or CPU load, increased latency, and inefficient energy consumption.

In contrast, the lower portion of FIG. 6 illustrates an optimized processing architecture in which patient data originating from hospital information systems, electronic medical records, historical records, and real-time sources as abstracted and governed by the Medical Data Governance engine, independent of any particular data acquisition hardware or transport mechanism, is first ingested and governed by the Medical Data Governance engine. The Medical Data Governance engine performs patient-specific data condensation, segmentation, and contextual filtering to generate multiple reduced, task-specific context representations rather than a single monolithic context vector. These prepared contexts are exposed through an MDG application programming interface and selectively delivered as distinct context components (C1, C2, C3, C4, C5, . . . Cn).

A supervisory orchestration process receives a clinician query (Q) and routes the query together with an appropriate reduced context component to a first large language model instance operating on a single GPU or CPU computational unit. This initial model instance performs query interpretation, decomposition, and routing decisions while operating on a constrained context, thereby minimizing computational overhead. Based on the query structure and required reasoning depth, the supervisory orchestration process distributes subtasks to multiple downstream large language model instances (L2, L3, L4, L5, . . . Ln), each operating on its own isolated GPU or CPU computational unit and each receiving only the specific context component (P2, P3, P4, P5, . . . Pn) necessary for its assigned task.

The outputs generated by the distributed large language model instances are collected as intermediate functional outputs (FA2, FA3, FA4, FA5, . . . FAn) and aggregated by a subsequent large language model instance configured for synthesis and consolidation. This aggregation stage produces a unified candidate response while avoiding the need for any single model instance to process the full patient context. A downstream validation stage is then invoked, in which a validation arbiter and associated validation model evaluate the synthesized output for correctness, consistency, and compliance prior to release.

By decomposing patient data into MDG-prepared, task-specific context components and distributing reasoning across multiple smaller computational units, the architecture illustrated in FIG. 6 significantly reduces peak GPU and CPU utilization, lowers memory bandwidth requirements, and minimizes redundant computation. This modular execution model enables selective activation of computational resources only when required, allowing fast-thinking model instances to handle lightweight or time-critical tasks while reserving slower, more resource-intensive processing for limited validation or synthesis stages.

The illustrated architecture further supports flexible deployment across cloud-based or on-premise execution environments, as each large language model instance operates independently and can be allocated to available computational resources based on cost, latency, or energy constraints. Because the Medical Data Governance engine pre-condenses and governs patient context prior to model execution, the system avoids repeated large-scale data transfer and unnecessary recomputation, thereby reducing operational cost and improving scalability across healthcare environments with varying resource availability.

Accordingly, FIG. 6 demonstrates a governance-driven, modular artificial intelligence execution architecture that achieves substantial energy efficiency and cost optimization by replacing monolithic large language model execution with distributed, context-constrained processing coordinated through the Medical Data Governance engine and supervisory orchestration logic.

FIG. 7: Governed Output Delivery and Task Execution Workflow illustrates an example embodiment of the final stages of query resolution, insight delivery, and task coordination within the insight platform, showing how clinician-initiated requests are processed through modular large language model execution, validated under governance control, and delivered as authorized outputs and task-related services through clinician-facing applications and Medical Data Governance services.

In the illustrated embodiment, one or more clinician-facing application interfaces (240) executing on a clinician device present multiple concurrent application contexts, including a first application interface (531), a second application interface (532), a third application interface (533), and a fourth application interface (534). Each application interface may correspond to a distinct workflow, patient view, or functional application and may generate a clinician query or request represented by a query input (Q) and an associated answer context (A). The clinician device further includes interaction and input elements (535) enabling submission of queries and receipt of responses.

Clinician queries (542) are transmitted to a first large language model instance (LM(1)), which receives the query input (Q) together with a context component (C1) (541) derived from governed patient data supplied by the Medical Data Governance engine (150). The first large language model instance (LM(1)) operates as an orchestration and routing model, generating structured sub-queries, decomposing the request, and invoking downstream processing through one or more application programming interfaces (API) (544). The first large language model instance produces intermediate outputs (545) and distributes processing tasks to a plurality of downstream large language model instances (L2, L3, L4, L5, . . . Ln), each of which receives a corresponding partial context component (C2, C3, C4, C5, . . . Cn) and associated parameters (P2, P3, P4, P5, . . . Pn) (551). Each downstream large language model instance executes independently through its own application programming interface (544) and generates intermediate functional outputs (FA2, FA3, FA4, FA5, . . . FAn) (555).

The intermediate functional outputs are aggregated and provided to a subsequent large language model instance (LM(2)), which also receives the original context component (C1) (541) and performs synthesis and consolidation of the distributed outputs into a candidate response. The synthesized output is forwarded to an aggregation and authorization stage (A) (560), the output of which is provided to a local orchestration and logic component (OLC) (221). The aggregation stage determines whether the synthesized output may proceed directly to delivery or should be subjected to additional validation.

In parallel or conditionally, the synthesized output may be routed to a validation pathway involving an additional large language model instance (LM(3)) (558) operating in conjunction with a validation arbiter (VA) (220). The validation arbiter evaluates the synthesized output for correctness, internal consistency, and compliance with governance rules. If the validation arbiter determines that a potential issue exists, a validation signal (V) (559) is generated, which may result in generation of a warning output, modification of the synthesized output, or suppression of the response. If no validation issue is detected, the output is permitted to proceed without modification.

Validated and authorized outputs are returned to the Medical Data Governance engine (150) via an application programming interface (544), where they may be associated with one or more downstream services, including task services, application services, data retrieval services, messaging services, metadata services, or other system services. The Medical Data Governance engine maintains governance control, auditability, and contextual binding of the outputs to the originating patient, clinician, and workflow.

The validated outputs are delivered back to the clinician-facing application interfaces (240), where they may be rendered as application outputs (245), updated answers (246), task-driven responses within application contexts (531-534), or contextual visualizations corresponding to the originating query, thereby enabling simultaneous interaction across multiple application contexts while preventing bypass of validation and governance controls.

FIG. 8: On-Demand, Context-Aware Insight Generation and Application Delivery illustrates an example embodiment of a seamless sign-on, contextual query handling, real-time conversational interaction, and application invocation workflow implemented by the insight platform. The figure depicts how clinician-initiated requests are received through a unified clinician-facing interface, how real-time conversational interactions are serialized and managed, and how requests are evaluated to determine whether they require a governed informational response or invocation of a clinical application, all without requiring separate manual authentication steps.

In the illustrated embodiment, a clinician user (255) interacts with the insight platform through one or more clinician-facing devices (240), such as a smartphone, tablet, or similar computing device. The clinician may submit a request (400) in text form or engage in a real-time conversational interaction via voice or other modalities. In some embodiments, real-time conversational interaction is facilitated by a real-time conversational AI agent (206), which operates within an real-time insight platform (205).

When real-time conversational interaction is used, clinician utterances, follow-up instructions, interruptions, or application requests are received by the real-time conversational AI agent (206) and processed by an input serialization and sequencing process (407). The serialization process (407) transforms continuous or asynchronous conversational interaction into a sequence of discrete, ordered user input units (207), ensuring that conversational turns are handled in series, that interruptions or deferred requests are preserved, and that each user input is processed independently under governance control. For each serialized user input unit (207), a corresponding system response (208) is generated, enabling consistent pairing of conversational inputs and outputs while maintaining modality continuity.

Serialized user inputs (207), whether originating from conversational interaction or from non-conversational input, are forwarded to an insight platform (200), which operates as an intermediary application layer between clinician-facing interfaces and downstream clinical services. The insight platform (200) evaluates each serialized input through a request classification step represented by a decision element (402), which determines whether the input corresponds to a direct informational query or an application-level request. This determination may be based on semantic interpretation of the input, contextual metadata associated with the clinician session, patient identifiers, or predefined application invocation triggers.

If a serialized user input (207) is determined to require a direct informational response, the insight platform (200) processes the request and returns a structured output answer (253) to the clinician-facing device (240). In the case of conversational interaction, the output may be rendered through the same modality used for input, such as synthesized speech via an audio interface (243, 244), while also optionally logging a textual transcription for auditability and later reference. The output answer (253) may include patient-specific clinical information, computed insights, or synthesized summaries presented within the same interface from which the request originated.

If a serialized user input (207) is determined to be an application request, the insight platform (200) initiates invocation of a corresponding clinical application or service while maintaining the clinician's authenticated session context. In this mode, the insight platform (200) facilitates seamless access to the requested application and returns application output (254) to the clinician-facing device (240). The application output (254) may include dynamically rendered application views, embedded content, or interactive interfaces displayed within the same clinician-facing environment, without requiring the clinician to re-authenticate or manually navigate to a separate system.

As illustrated, the workflow supports multiple serialized request-response cycles within a single authenticated session, including conversational interactions that may involve interruptions, follow-on requests, or deferred actions. Each serialized input (207) is processed independently, and each corresponding output (208) is delivered only after appropriate downstream processing, ensuring that conversational responsiveness does not bypass governance, reasoning, or validation mechanisms described elsewhere in the system.

The configuration illustrated in FIG. 8 enables clinicians to submit contextual questions and application requests through a unified interface, engage in real-time conversational interaction when desired, and receive either direct informational outputs or application-driven content in a session-preserving manner. By serializing conversational input and integrating request classification with seamless sign-on and application invocation, the insight platform reduces interaction friction, minimizes authentication overhead, and supports efficient, governed clinical workflow execution at the point of care.

PRIOR ART AND DISTINCTIONS

Various systems and technologies have addressed individual aspects of clinical information access, conversational interfaces, natural language processing, data ingestion, or decision support. However, such systems typically operate on isolated data sources, lack governance-controlled reasoning pipelines, or are not architected to combine real-time patient context, modular reasoning, and validation-controlled output delivery within a single integrated platform. The present disclosure describes a system architecture and operational framework that integrates these elements in a manner not taught or suggested by known systems.

Conventional clinical reference tools and knowledge repositories provide curated medical content, guideline summaries, or literature-based information intended for manual consultation. Such systems generally require explicit navigation or search, do not ingest or validate real-time patient data streams, and do not generate outputs conditioned on dynamically governed patient context. Further, these tools typically operate without session continuity, longitudinal interaction memory, or real-time feedback loops that adapt outputs as underlying patient data changes.

Separately, general-purpose conversational or natural language interaction systems are designed to interpret user input and generate responses in broad, non-domain-specific contexts. These systems are not configured to operate on governed clinical data, do not enforce access control, provenance tracking, or regulatory constraints, and do not support validation-controlled output release in environments where safety, auditability, and accountability are required. As such, they are not suitable for integration into regulated clinical workflows.

Certain prior technologies disclose aspects of audio interaction, duplex communication, or dialogue management. Other systems disclose ingestion of medical device data or application of artificial intelligence to healthcare datasets. However, these disclosures typically address isolated components—such as data transport, signal processing, or rule-based analysis—without describing a coordinated architecture in which governed data preparation, modular reasoning agents, orchestration logic, and non-bypassable validation are combined into a unified operational pipeline.

Some prior systems apply artificial intelligence models to healthcare data but rely on static compliance checks or post hoc auditing. In contrast, the present invention employs a Medical Data Governance engine that actively constrains data exposure, structures context for reasoning, and enforces policy and provenance at the time of reasoning rather than solely after output generation. Validation is performed as an integral stage of the reasoning pipeline, rather than as a downstream or optional step.

Likewise, prior disclosures of modular or agent-based artificial intelligence systems do not teach or suggest a supervisory orchestration component that dynamically selects, sequences, and aggregates reasoning tasks across multiple agents while coordinating validation dependencies and controlling output authorization. The present invention's architecture separates reasoning generation from authorization, ensuring that candidate outputs produced by one or more models or agents cannot be delivered without affirmative validation under governance constraints.

In contrast to systems that provide static alerts, fixed dashboards, or one-time analysis, the present invention supports iterative interaction in which clinician requests, governed context, intermediate outputs, and validation outcomes may evolve over time. This interaction is mediated through defined interfaces and controlled workflows, preserving traceability and auditability while allowing context-sensitive refinement without bypassing governance or authorization controls.

Accordingly, while elements such as speech recognition, language models, device connectivity, or clinical data repositories are known individually, the present invention does not merely aggregate these elements. Rather, it defines a specific technical architecture in which governed data preparation, modular reasoning execution, supervisory orchestration, and validation-controlled delivery are integrated into a single platform. This combination enables technical effects including controlled exposure of clinical context, reduction of unvalidated output propagation, and consistent enforcement of policy and safety constraints across heterogeneous data sources and reasoning components.

The disclosed system is therefore distinguished not by the mere use of artificial intelligence or conversational interfaces, but by the manner in which these components are constrained, coordinated, and validated within a governance-driven architecture. The resulting platform is configured to operate across diverse clinical environments, data availability conditions, and deployment models while maintaining consistent control over data integrity, reasoning scope, and output authorization.

NON-OBVIOUSNESS JUSTIFICATION

The present invention represents a non-obvious technical advancement in the field of healthcare information systems and artificial intelligence-enabled clinical support. The disclosed system is not directed to the mere application of known algorithms or generic language models to medical data, nor to the automation of clinical judgment. Instead, it defines a specific system architecture and operational framework that integrates governed data preparation, modular reasoning execution, supervisory orchestration, and validation-controlled output delivery in a manner not taught or suggested by known systems.

While individual components such as data repositories, artificial intelligence models, conversational interfaces, or device integration mechanisms are known in isolation, the present invention is distinguished by the manner in which these components are constrained, coordinated, and interdependent. In particular, the invention introduces a governance-centric architecture in which patient-related data is structured, scoped, and authorized prior to reasoning, and in which candidate outputs generated by one or more reasoning components are subject to non-bypassable validation prior to delivery. This architectural separation between data governance, reasoning generation, and authorization is not a predictable extension of existing systems.

The disclosed system further departs from prior approaches by supporting controlled, iterative processing over evolving data states. Rather than operating on static datasets or precompiled summaries, the system prepares governed context representations at multiple temporal resolutions and selectively supplies task-specific context components to reasoning models or agents under orchestration control. This enables technical effects such as reduced computational load, controlled data exposure, and consistent enforcement of policy constraints across heterogeneous reasoning pathways. Such effects arise from the coordinated interaction of the disclosed components rather than from any single algorithm or model.

Non-obviousness is further supported by the system's use of a supervisory orchestration component that dynamically decomposes requests, routes governed context, aggregates intermediate outputs, and enforces dependencies between reasoning and validation stages. Known systems that employ multiple models or agents do not teach this form of centralized orchestration combined with validation-controlled release semantics, particularly in environments subject to regulatory, auditability, and safety constraints.

In addition, the invention defines a validation arbiter that operates as an authorization authority distinct from the reasoning components themselves. Candidate outputs may be modified, suppressed, or conditionally released based on consistency checks, policy constraints, or safety criteria, without permitting direct delivery from reasoning models. This separation of generation and authorization produces a technical control structure that is fundamentally different from systems that rely on post-hoc review, static rule engines, or unbounded model output.

The non-obvious nature of the invention is also reflected in its ability to operate across diverse deployment environments, including settings with intermittent connectivity, heterogeneous data sources, or incomplete records, while maintaining consistent governance and validation behavior. This is achieved through architectural design choices—such as context segmentation, temporal abstraction, and modular execution—that would not be apparent from systems focused solely on centralized data lakes, monolithic analytics pipelines, or consumer-grade conversational interfaces.

Importantly, the present invention does not assert that automated outputs replace clinical judgment or establish a clinical practice workflows. Rather, it provides a technical framework for generating, constraining, and delivering information outputs derived from governed data and controlled reasoning processes. Any clinical interpretation or action remains external to the system and under the control of a human user. This distinction further underscores that the invention is directed to a technical solution for managing complex data-driven workflows, not to an abstract idea or a method of medical treatment.

Taken as a whole, the disclosed architecture reflects a non-obvious combination of elements that cooperate to achieve technical effects not realized by prior systems: controlled exposure of patient context, modular and orchestrated reasoning execution, non-bypassable validation, and audit-ready output delivery. The claimed invention therefore represents more than the predictable use of known components according to their established functions and satisfies the requirements of non-obviousness under applicable patent law.

The invention claimed is:

1. A computer-implemented system for generating governed clinical insights, comprising:

one or more processors;

non-transitory computer-readable memory storing instructions that, when executed by the one or more processors, cause the system to perform operations comprising:

(a) a medical data governance (MDG) engine configured to (i) receive heterogeneous patient-related data originating from one or more clinical information systems, medical devices, or clinician inputs, (ii) validate, normalize, and timestamp said data under predefined governance rules, and (iii) generate structured, context-constrained data representations associated with an identified patient and clinical episode, wherein the same MDG engine is further configured to apply governance rules to validate, filter, and contextualize the patient-related data and to make governed context available to a reasoning layer including one or more modular artificial intelligence agents;

(b) a reasoning layer comprising one or more artificial-intelligence models, including at least one large-language model (LLM), the reasoning layer being configured to generate one or more candidate clinical outputs using the structured, context-constrained data representations supplied by the MDG engine;

(c) a supervisory orchestration component configured to manage reasoning flow by selecting, sequencing, and coordinating execution of a plurality of modular artificial intelligence agents, wherein the modular artificial intelligence agents operate under coordination of the supervisory orchestration component to generate intermediate outputs based on governed context;

(d) a validation arbiter operatively coupled to receive candidate clinical outputs produced by the reasoning layer and the modular artificial intelligence agents, and configured to (i) evaluate said candidate clinical outputs for consistency, validity, and compliance with governance constraints enforced by the MDG engine, and (ii) selectively authorize, modify, or suppress delivery of the candidate clinical outputs;

(e) a clinician interaction interface configured to present only clinical outputs authorized by the validation arbiter to an authenticated user;

wherein no candidate clinical output generated by the reasoning layer or modular artificial intelligence agents is presented to the clinician interaction interface unless first evaluated by the validation arbiter in accordance with governance enforced by the MDG engine.

2. The system of claim 1,
wherein the reasoning layer is configured to execute a fast-response reasoning mode for time-sensitive clinical situations and a deliberative reasoning mode for context-intensive clinical analysis,
and wherein outputs from both modes are subject to evaluation by the validation arbiter prior to delivery.

3. The system of claim 2,
wherein the validation arbiter is configured to reconcile candidate clinical outputs generated by the fast-response reasoning mode and the deliberative reasoning mode before authorizing delivery.

4. The system of claim 1,
wherein the reasoning layer comprises a plurality of large-language models configured to generate candidate clinical outputs corresponding to different temporal scopes, data granularities, or clinical contexts.

5. The system of claim 4,
wherein the validation arbiter is configured to compare candidate clinical outputs generated by different large-language models and suppress outputs exhibiting inconsistency or policy non-compliance.

6. The system of claim 1,
wherein the clinician interaction interface is configured to render authorized clinical outputs as structured application outputs comprising at least one of trend visualizations, diagnostic summaries, or device-specific data views.

7. The system of claim 1,
wherein the medical data governance (MDG) engine is operatively coupled to one or more edge or intermediary data-acquisition components by which patient-related data is made available for preprocessing prior to ingestion,
and wherein the preprocessing is constrained by governance rules enforced by the MDG engine.

8. The system of claim 7,
wherein the preprocessing comprises at least one of normalization, buffering, rate adaptation, or protocol translation,
and wherein the preprocessed data is forwarded to the MDG engine together with provenance metadata.

9. The system of claim 8,
wherein the MDG engine applies governance rules to selectively admit, discard, or defer preprocessed data prior to generation of structured, context-constrained data representations.

10. The system of claim 1,
wherein the MDG engine maintains a governed conversational context associated with an identified patient and clinical episode,
the governed conversational context comprising previously authorized clinical outputs and clinician interactions.

11. The system of claim 10,
wherein the reasoning layer generates candidate clinical outputs using the governed conversational context as an input constraint.

12. The system of claim 11,
wherein the validation arbiter evaluates candidate clinical outputs for consistency with the governed conversational context before authorizing delivery.

13. The system of claim 1,
wherein, in addition, for at least a subset of candidate clinical outputs classified as high-risk outputs, no such candidate clinical output is presented to the clinician interaction interface unless first evaluated and authorized by the validation arbiter.

14. The system of claim 13,
wherein the high-risk outputs comprise at least one of medication-related recommendations, contraindication determinations, dosing guidance, safety alerts, or outputs associated with potential patient harm if incorrect.

15. The system of claim 1,
wherein the clinician interaction interface comprises a real-time conversational interaction component configured to receive clinician input in a real-time conversational modality including voice-based input, to maintain an active conversational session supporting interruption handling and prioritization, and to transform conversational input into one or more structured user input units supplied to the supervisory orchestration component for governed processing,
wherein the real-time conversational interaction component may request additional information when conversational input is incomplete or contextually insufficient,
and wherein the real-time conversational interaction component does not independently generate, authorize, modify, or release clinical outputs for presentation to the clinician.

16. The system of claim 15,
wherein the real-time conversational interaction component is further configured to:
(a) serialize conversational clinician inputs received during the active conversational session into a sequence of discrete, ordered input units;
(b) associate each serialized input unit with a corresponding candidate clinical output generated by the reasoning layer; and
(c) control presentation of conversational outputs to the clinician in an ordered manner corresponding to the serialized input units,
wherein each conversational output is presented to the clinician only after validation and authorization by the validation arbiter in accordance with claim 1, and wherein serialization prevents interruption, reordering, or bypass of governance, orchestration, or validation mechanisms.

17. A computer-implemented method for generating governed clinical insights, comprising:
(a) receiving heterogeneous patient-related data originating from one or more clinical information systems, medical devices, or clinician inputs;
(b) validating, normalizing, and timestamping the patient-related data under predefined governance rules using a medical data governance (MDG) engine, and generating structured, context-constrained data representations associated with an identified patient and clinical episode;
(c) generating, by a reasoning layer comprising one or more artificial-intelligence models including at least one large-language model (LLM), one or more candidate clinical outputs using the structured, context-constrained data representations supplied by the MDG engine;
(d) performing, by a plurality of modular AI agents operating under coordination of a supervisory agent, specialized reasoning tasks contributing to the candidate clinical outputs;
(e) evaluating, by a validation arbiter operating downstream of the modular AI agents, the candidate clinical outputs for consistency, validity, and compliance with governance constraints enforced by the MDG engine;

(f) selectively authorizing, modifying, or suppressing the candidate clinical outputs based on the evaluation performed by the validation arbiter; and (g) presenting, via a clinician interaction interface, only candidate clinical outputs authorized by the validation arbiter to an authenticated user;

wherein no candidate clinical output generated by the reasoning layer or the modular AI agents is presented unless first evaluated by the validation arbiter in accordance with governance enforced by the MDG engine.

18. The method of claim 17, wherein generating the one or more candidate clinical outputs comprises executing a fast-response reasoning mode for time-sensitive clinical situations and a deliberative reasoning mode for context-intensive clinical analysis, and wherein evaluating the candidate clinical outputs comprises reconciling outputs produced by the fast-response reasoning mode and the deliberative reasoning mode prior to authorizing presentation.

19. The method of claim 17, wherein generating the one or more candidate clinical outputs comprises invoking a plurality of large-language models corresponding to different temporal scopes, data granularities, or clinical contexts, and wherein evaluating the candidate clinical outputs comprises comparing outputs generated by different large-language models and suppressing outputs exhibiting inconsistency or governance policy non-compliance.

20. The method of claim 17, further comprising maintaining a governed conversational context associated with the identified patient and clinical episode, the governed conversational context comprising previously authorized clinical outputs and clinician interactions, and wherein generating the one or more candidate clinical outputs comprises using the governed conversational context as an input constraint.

21. The method of claim 17, further comprising generating, upon authorizing a candidate clinical output, an authorization record comprising an authorization state and release-evidence metadata identifying at least one governance condition evaluated, and presenting the authorized clinical output together with at least a portion of the authorization record.

22. The method of claim 17, wherein, in addition, for at least a subset of candidate clinical outputs classified as high-risk outputs, the method further comprises preventing presentation of such candidate clinical outputs to the clinician interaction interface unless first evaluated and authorized by the validation arbiter.

23. The method of claim 22, wherein the high-risk outputs comprise at least one of medication-related recommendations, contraindication determinations, dosing guidance, safety alerts, or outputs associated with potential patient harm if incorrect.

24. The method of claim 17, wherein receiving clinician input further comprises receiving clinician interaction through a real-time conversational clinical interface configured to support voice-based and multimodal interaction, and wherein the method further comprises:

(a) maintaining an active conversational session with the clinician;

(b) dynamically managing conversational flow including interruptions, follow-on requests, deferred actions, and priority handling; and (c) transforming conversational interaction into one or more structured, discrete user input units supplied to the supervisory orchestration component for governed processing, without independently generating, validating, authorizing, or releasing clinical outputs for presentation to the clinician.

25. The method of claim 24, wherein transforming conversational interaction further comprises:

(a) serializing conversational clinician inputs into an ordered sequence of discrete input units;

(b) associating each discrete input unit with a corresponding candidate clinical output generated by the reasoning layer; and (c) temporally controlling presentation of conversational outputs to the clinician such that each output is presented only after validation and authorization and in an order corresponding to the serialized input units, thereby preserving conversational ordering, interruption handling, and deferred requests without bypassing governance, orchestration, or validation mechanisms.

26. A non-transitory computer-readable medium storing instructions that, when executed by one or more processors, cause a computer-implemented system to perform operations comprising:

(a) receiving heterogeneous patient-related data under governance control from one or more electronic healthcare information systems, medical devices, or clinician inputs;

(b) applying, by a medical data governance (MDG) engine, predefined governance rules to validate, normalize, timestamp, and contextualize the patient-related data and to generate structured, context-constrained data representations associated with an identified patient and clinical episode;

(c) making the structured, context-constrained data representations available to a reasoning layer comprising one or more artificial intelligence models, including at least one large language model (LLM);

(d) generating, by the reasoning layer, one or more candidate clinical outputs based on the structured, context-constrained data representations;

(e) coordinating execution of a plurality of modular artificial intelligence agents under control of a supervisory orchestration component to produce intermediate outputs based on the governed context;

(f) evaluating, by a validation arbiter, the candidate clinical outputs for consistency, validity, and compliance with governance constraints enforced by the MDG engine; and (g) selectively authorizing, modifying, or suppressing delivery of the candidate clinical outputs such that only authorized clinical outputs are presented via a clinician interaction interface.

27. The non-transitory computer-readable medium of claim 26, wherein the instructions further cause the system to prevent presentation of at least a subset of candidate clinical outputs classified as high-risk outputs unless first evaluated and authorized by the validation arbiter.

28. The non-transitory computer-readable medium of claim 27, wherein the high-risk outputs comprise at least one of medication-related recommendations, contraindication determinations, dosing guidance, safety alerts, or outputs associated with potential patient harm if incorrect.

* * * * *